United States Patent
Frieling et al.

(10) Patent No.: US 10,059,996 B2
(45) Date of Patent: Aug. 28, 2018

(54) SUSCEPTIBILITY TO AND STRATIFICATION FOR MONOAMINERGIC ANTIDEPRESSANTS

(71) Applicants: MEDIZINISCHE HOCHSCHULE HANNOVER, Hannover, DE (US); UNIVERSITÄTSMEDIZIN DER JOHANNES-GUTENBERG-UNIVERSITÄT MAINZ, Mainz (DE)

(72) Inventors: Helge Frieling, Hannover (DE); André Tadic, Flörsheim am Main (DE); Stefan Bleich, Uetze (OT Obershagen) (DE); Klaus J. Lieb, Mainz (DE)

(73) Assignees: Medizineische Hochschule Hannover, Hannover (DE); Universitätsmedizin der Johannes-Gutenberg-Universität Mainz, Mainz (DE)

( * ) Notice: Subject to any disclaimer, the term of this patent is extended or adjusted under 35 U.S.C. 154(b) by 42 days.

(21) Appl. No.: 14/406,983

(22) PCT Filed: May 8, 2013

(86) PCT No.: PCT/EP2013/059677
§ 371 (c)(1),
(2) Date: Dec. 10, 2014

(87) PCT Pub. No.: WO2013/185987
PCT Pub. Date: Dec. 19, 2013

(65) Prior Publication Data
US 2015/0184242 A1 Jul. 2, 2015

(30) Foreign Application Priority Data
Jun. 11, 2012 (EP) .................................... 12171541

(51) Int. Cl.
*C12Q 1/68* (2018.01)
*C12Q 1/6883* (2018.01)
*G01N 33/68* (2006.01)

(52) U.S. Cl.
CPC ....... *C12Q 1/6883* (2013.01); *G01N 33/6893* (2013.01); *C12Q 2600/106* (2013.01); *C12Q 2600/154* (2013.01); *G01N 2333/475* (2013.01); *G01N 2440/12* (2013.01); *G01N 2800/304* (2013.01); *G01N 2800/52* (2013.01)

(58) Field of Classification Search
None
See application file for complete search history.

(56) References Cited

U.S. PATENT DOCUMENTS

2009/0053706 A1* 2/2009 Laird ................... C12Q 1/6886
435/6.12
2011/0237537 A1* 9/2011 Lombard ............. C12Q 1/6883
514/46

FOREIGN PATENT DOCUMENTS

WO 2007084734 A2 7/2007
WO 2012017867 A1 2/2012

OTHER PUBLICATIONS

Ehrlich et al. (2002 Oncogene vol. 21 p. 5400.*
Walsh et al teaches (Genes & Development (1999) vol. 13, pp. 26-36).*
Chang et al. (PNAS Dec. 2010 vol. 107 p. 21836-21841).*
Brooks et al. (Cancer Causes Control Nov. 2009 vol. 20 p. 1539).*
Andre Tadic et al: "The early non-increase of serum BDNF predicts failure of antidepressant treatment in patients with major depression: A pilot study", Progress in Neuro-Psychopharmacology & Biological Psychiatry, Oxford, GB, vol. 35, No. 2, Aug. 15, 2010 (Aug. 15, 2010), pp. 415-420, XP028156605.
Andre Tadic, et al: "Peripheral blood and neuropsychological markers for the onset of action of antidepressant drugs in patients with Major Depressive Disorder", BMC Psychiatry, Biomed Central, London, GB, vol. 11, No. 1,Jan. 26, 2011 (Jan. 26, 2011), p. 16, XP021087383.
Keller, S., et al: "Increased BDNF Promoter Methylation in the Wernicke Area of Suicide Subjects", Arch Gen Psychiatry, vol. 67, No. 3, Mar. 2010 (Mar. 2010), pp. 258-267, XP002686166.
Written Opinion in parent PCT application PCT/EP2013/059677.

* cited by examiner

*Primary Examiner* — Katherine D Salmon
(74) *Attorney, Agent, or Firm* — Michele M. Wales; InHouse Patent Counsel, LLC

(57) ABSTRACT

The present invention relates to a method for predicting the non-response or response to a monoaminergic antidepressant of a patient to be treated with a monoaminergic antidepressant comprising the steps: (i) determining the DNA-methylation status of a brain-derived neurotrophic factor (BDNF)-gene promoter in a sample of said patient; (ii) attributing a hypomethylation of said BDNF-gene promoter to the non-response to a monoaminergic antidepressant of said patient; and (iii) attributing normal methylation or hypermethylation of said BDNF-gene promoter to the response to a monoaminergic antidepressant of said patient. Furthermore, a kit and the use of a kit in said method is disclosed.

13 Claims, 9 Drawing Sheets

Figure 1:
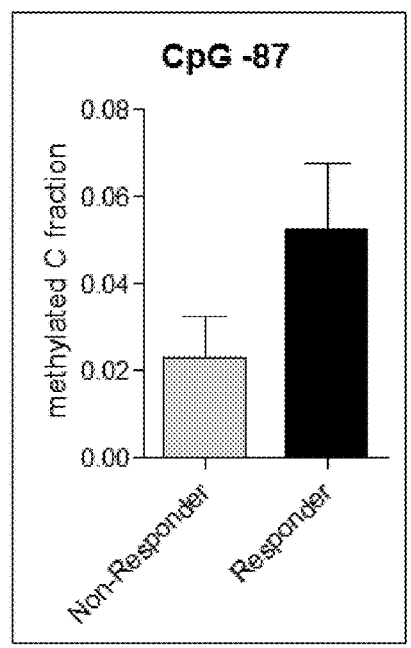
Figure 1:
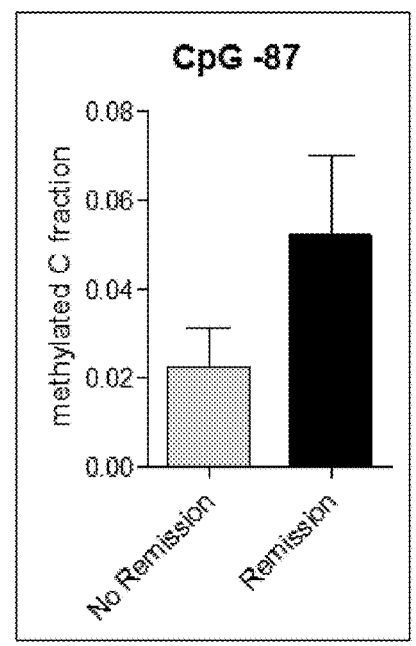

Specification includes a Sequence Listing.

A

B

A

B-1

B-2

A

B

C

D-1

D-2

E

SUSCEPTIBILITY TO AND STRATIFICATION FOR MONOAMINERGIC ANTIDEPRESSANTS

The present application relates to the field of medicine, particularly to personalized medicine and molecular biomarkers. The application relates to a method for predicting the response or non-response of a patient to an antidepressant, particularly for predicting the response or non-response to a monoaminergic antidepressant using epigenetic markers at the BDNF gene. The invention further relates to a method of treating a patient suffering from or suspected of suffering from a depression or a depression related disease with a monoaminergic antidepressant, said method comprising the steps of identifying a patient with normal methylation or hypermethylation of the BDNF-gene promoter, and administering said monoaminergic antidepressant to said patient. The invention also relates to a method for the determination of suitability of a given individual, in particular a human patient, for the treatment with (a) monoaminergic antidepressant(s) whereby this method comprises the definition of the DNA-methylation status of a BDNF-gene promoter in a (biological) sample of said patient and wherein hypomethylation of said BDNF-gene promoter indicates that the individual is a non-responder to monoaminergic antidepressants and wherein a normal methylation or hypermethylation of said BDNF-gene promoter indicates a responder to monoaminergic antidepressants. A non-responder to monoaminergic antidepressants in accordance with this invention is treated with an alternative medical and/or psychological intervention/therapy.

The present invention relates to means and methods for stratifying patients for the medical intervention with (a) monoaminergic antidepressant(s).

Depression is a common mental disorder, characterized by sadness, loss of interest or pleasure, feelings of guilt or low self-worth, disturbed sleep or appetite, low energy and poor concentration. Depression often becomes chronic or recurrent, substantially impairing an individual's ability to cope with daily life. At its most severe, depression can lead to suicide. In Germany 20% to 25% of adults suffer from a depression at least once during lifetime. The treatment of depression usually includes psychotherapy, sociotherapy and/or pharmacotherapy. Most commonly used pharmacotherapy comprises the treatment with monoaminergic antidepressants, e.g. comprising fluoxetine (Prozac®). All of these methods show efficiency depending on the patient treated. However, there is a need for a tool that allows deciding which therapy to use for which patient. An early and sufficient therapy is of extraordinary importance in order to prevent the patient from chronic depression or recurrence. Current data show that only half of the patients respond the first chosen therapy. The portion of patients responding to the second or further therapy is even lower. Up to now, the response of a patient to the therapy of depression cannot be determined beforehand but is only possible by clinical evaluation after two to four weeks of treatment. No marker is available for sufficient determination of the response to the treatment of depression. Hence, there is a need for a method allowing the prediction of the response or non-response to therapeutic treatment of a patient suffering from depression.

In the last decades major efforts have been made to identify a biomarker for improved diagnosis, subtyping and prediction of response to therapy of depression and other mood disorders. Several neurotrophic factors were discussed in this connection, e.g. brain-derived neurotrophic factor (BDNF), glia-derived neurotrophic factor (GDNF), as well as cytokines, insulin-like growth factor 1 (IGF-1) or endocrinological parameters as e.g. hypothalamo-pituitary-adrenal gland (HPA)-axis hormones. Until today none of the markers is sufficiently specific. Moreover, most of the studies revealed inconclusive and inconsistent results. Likewise, genetic tests did not produce replicable results. Therefore, the current strategy is to monitor the dynamics of different parameters within the first days and weeks of the treatment of depression in order to allow an early change in therapy if the patient does not respond.

A widely known treatment of depression is the administration of antidepressants, e.g. monoaminergic antidepressants. Predictors of treatment response to such antidepressants have been searched and discussed for some time and include clinical, cognitive, psychophysiological, neuroimaging and genetic predictors (Kemp et al. (2008), "Improving the Prediction of Treatment Response in Depression: Integration of Clinical, Cognitive, Psychophysiological, Neuroimaging, and Genetic Measures", CNS Spectr 13:12, 1066). However, until today the integration of different methods to predict treatment response is suggested in order to give a sufficiently specific prediction (Kemp et al. (2008), Improving the Prediction of Treatment Response in Depression: Integration of Clinical, Cognitive, Psychophysiological, Neuroimaging, and Genetic measures, CNS Spectr 13:12, 1066). However, antidepressants are also administered to patients suffering from other disorders than depression and are cured based on the same mechanism. For such diseases a method for predicting the response or non-response to a monoaminergic antidepressant is also not known and the provision of such is a problem underlying the present invention.

The brain-derived neurotrophic factor (BDNF) has been discussed as a diagnostic marker and modulator for the presence of a depression and other mental disorders like impulsive aggression in borderline personality disorders. The BDNF locus spans about 70 kb, consists of 11 exons, and codes for 15 different transcripts including different exons of the locus. The expression of the transcripts is regulated by different promoters upstream of the respective 5'-exons, depending on the start of transcription (Pruunsild, et al. (2007), Dissecting the human BDNF locus: Bidirectional transcription, complex splicing and multiple promoters, Genomics 90, 397-406). Epigenetic markers, i.e. methylation status of the DNA or modification of histones, are commonly used in the field of oncology. First studies revealed that the methylation status of different genes is indicative for the presence of depression. One study indicated a correlation between the methylation status of the BDNF-gene exon-I promoter but not BDNF-gene exon-IV promoter and the presence of depression (Fuchikami et al. (2011); DNA Methylation Profiles of the Brain-Derived Neurotrophic Factor (BDNF) Gene as a Potent Diagnostic Biomarker in Major Depression. PLos ONE 6(8):e23881). Another study indicated the tissue specific hypermethylated BDNF exon-IV promoter in the Wernicke's area in suicide subjects (Keller et al. (2010), Arch Gen Psychiatry; 67(3), 258).

All strategies currently applied to monitor the response to the treatment of a patient suffering from depression have the disadvantage that a conclusion of the efficacy of said treatment may only be set after the treatment has been started. Hence, one problem underlying the present invention is the provision of a method allowing the prediction of the response or non-response to treatment of depression of a patient before the start of said treatment. The provision of a method allowing the specific prediction of the response to antidepressants, especially to monoaminergic antidepressants, is of greatest interest and a problem underlying the invention as described herein below.

The invention, accordingly, relates to the following:

1. A method for predicting the non-response or response to a monoaminergic antidepressant of a patient to be treated with a monoaminergic antidepressant comprising the steps:
   i) determining the DNA-methylation status of a brain-derived neurotrophic factor (BDNF)-gene promoter in a sample of said patient;
   ii) attributing a hypomethylation of said BDNF-gene promoter to the non-response to a monoaminergic antidepressant of said patient; and
   iii) attributing normal methylation or hypermethylation of said BDNF-gene promoter to the response to a monoaminergic antidepressant of said patient.
2. Method according to item 1, whereby said BDNF-gene promoter is BDNF-gene exon-IV promoter (SEQ ID NO. 1).
3. Method according to item 2, whereby hypomethylation of the BDNF-gene exon-IV promoter at at least one of a CpG island selected from the group consisting of CpG−87, CpG−148, CpG−111, CpG+18, CpG−66, CpG−58, CpG−35, CpG−39, CpG−24, CpG−11, CpG+20, CpG+36, CpG+42, CpG+51, and CpG+54 is attributed to the non-response to a monoaminergic antidepressant of said patient, and normal methylation or hypermethylation at at least one of a CpG island selected from the group consisting of CpG−87, CpG−148, CpG−111, CpG+18, CpG−66, CpG−58, CpG−35, CpG−39, CpG−24, CpG−11, CpG+20, CpG+36, CpG+42, CpG+51, and CpG+54 is attributed to the response to a monoaminergic antidepressant of said patient; preferably hypomethylation at CpG−87 is attributed to the non-response to a monoaminergic antidepressant of said patient, and normal methylation or hypermethylation at CpG−87 is attributed to the response to a monoaminergic antidepressant of said patient.
4. Method according to any one of items 1 to 3, whereby a methylated C fraction of less than 0.05 is attributed to the non-response of said patient to a monoaminergic antidepressant, preferably a methylated C fraction of less than 0.04, more preferably a methylated C fraction of 0.03 or less is attributed to the non-response of said patient to a monoaminergic antidepressant.
5. Method according to any one of items 1 to 4, whereby the monoaminergic antidepressant comprises a compound from the group consisting of selective serotonin reuptake inhibitors (SSRI), selective serotonin and noradrenaline reuptake inhibitors (SNRI) selective noradrenaline and dopamine reuptake inhibitors, selective norepinephrine-dopamine reuptake inhibitors, monoamine oxidase inhibitors, tricyclic antidepressants, and other monoaminergic antidepressants, preferably the monoaminergic antidepressant is selected from the group consisting of venlafaxin, sertralin, mirtazapin, escitalopram, citalopram, fluoxetine, paroxetin, duloxetin, bupropion, amitriptylin, clomipramin, trimipramin, tranylcypromin.
6. Method according to any one of items 1 to 5, wherein the methylation status is determined using a technique selected from the group consisting of bisulfite sequencing, pyrosequencing, MALDI-TOF, methylation sensitive enzymatic digestion, and qMSP.
7. Method according to any one of items 1 to 6, wherein the steps are performed before administration of a monoaminergic antidepressant.
8. Method according to any one of items 1 to 7, whereby the sample is selected from the group consisting of blood, serum, plasma, saliva, sputum and cerebrospinal fluid.
9. Method according to any one of items 1 to 8, wherein the patient is suspected to have or is suffering from a disease selected from the group consisting of depression, major depressive disorder, mild depression, panic disorder, social anxiety disorder, social phobia, bulimia nervosa, obsessive-compulsive disorder, post-traumatic stress disorder, and generalized anxiety disorder.
10. A method for stratifying a patient for treatment with (a) monoaminergic antidepressant(s), said method comprising steps (i) to (iii) of items 1 to 9;
    wherein hypomethylation of said BDNP-gene promoter indicates that the patient is not suitable for therapy with (a) monoaminergic antidepressant(s) and that the patient should be treated with an alternative therapy to monoaminergic antidepressants; and
    wherein normal methylation or hypermethylation f said BDNF-gene promoter indicates that the patient is to be treated with (a) monoaminergic antidepressant(s).
11. The method for stratifying a patient for treatment with (a) monoaminergic antidepressant(s) of item 10, wherein hypomethylation of the BDNF-gene promoter indicates that the patient should be treated with an alternative therapy to monoaminergic antidepressants, like, inter alia, psychotherapy or electro convulsive therapy (ECT).
12. The method for stratifying of a patient for treatment with (a) monoaminergic antidepressant(s) of item 10, wherein normal or hypermethylation of the BDNF-gene promoter indicates that the patient is to be treated with (a) monoaminergic antidepressant(s).
13. A kit for determining whether a patient suffering from depression is a non-responder to monoaminergic antidepressant comprising:
    means for determining the methylation status of DNA; and
    at least one primer pair for amplifying a BDNF-gene promoter or a fragment thereof.
14. Kit according to item 13, wherein the at least one primer pair is suitable for amplifying the BDNF-gene exon-IV promoter, preferably for amplifying a fragment of said promoter, wherein said fragment comprises at least CpG island CpG−87.
15. Kit according to item 13 or 14, wherein the means for determining the methylation status of DNA is bisulfite, preferably sodium bisulfite.
16. Kit according to any one of items 13 to 15, wherein the primer pair for amplifying the BDNF-gene promoter or a fragment thereof have the sequence of SEQ ID NO. 2 and SEQ ID NO. 4.
17. Kit according to any one of items 13 to 16 further comprising a manual, wherein the manual comprises control data for determining whether the DNA of a BDNF-gene promoter is hypomethylated, normal methylated or hypermethylated.
18. Use of a kit according to any one of items 13 to 17 in a method according to any one of items 1 to 12.
19. A method for predicting the non-response or response to a monoaminergic antidepressant of a patient to be treated with a monoaminergic antidepressant comprising the steps:
    i) amplifying a BDNF-gene promoter or a fragment thereof by using at least one primer pair and determining the DNA-methylation status of the BDNF-gene promoter in a sample of said patient;

ii) attributing a hypomethylation of said BDNF-gene promoter to the non-response to a monoaminergic antidepressant of said patient; and iii) attributing normal methylation or hypermethylation of said BDNF-gene promoter to the response to a monoaminergic antidepressant of said patient.

20. Method according to item 19, wherein the at least one primer pair is suitable for amplifying the BDNF-gene exon-IV promoter, preferably for amplifying a fragment of said promoter, wherein said fragment comprises at least CpG island CpG−87.

21. Method according to item 19 or 20, wherein the primer pair for amplifying the BDNF-gene promoter or a fragment thereof have the sequence of SEQ ID NO. 2 and SEQ ID NO. 4.

22. Method according to any one of items 19 to 21, whereby said BDNF-gene promoter is BDNF-gene exon-IV promoter (SEQ ID NO. 1).

23. Method according to item 22, whereby hypomethylation of the BDNF-gene exon-IV promoter at at least one of a CpG island selected from the group consisting of CpG−87, CpG−148, CpG−111, CpG+18, CpG−66, CpG−58, CpG−35, CpG−39, CpG−24, CpG−11, CpG+20, CpG+36, CpG+42, CpG+51, and CpG+54 is attributed to the non-response to a monoaminergic antidepressant of said patient, and normal methylation or hypermethylation at at least one of a CpG island selected from the group consisting of CpG−87, CpG−148, CpG−111, CpG+18, CpG−66, CpG−58, CpG−35, CpG−39, CpG−24, CpG−11, CpG+20, CpG+36, CpG+42, CpG+51, and CpG+54 is attributed to the response to a monoaminergic antidepressant of said patient; preferably hypomethylation at CpG−87 is attributed to the non-response to a monoaminergic antidepressant of said patient, and normal methylation or hypermethylation at CpG−87 is attributed to the response to a monoaminergic antidepressant of said patient.

24. Method according to any one of items 19 to 23, whereby a methylated C fraction of less than 0.05 is attributed to the non-response of said patient to a monoaminergic antidepressant, preferably a methylated C fraction of less than 0.04, more preferably a methylated C fraction of 0.03 or less is attributed to the non-response of said patient to a monoaminergic antidepressant.

25. Method according to any one of items 19 to 24, whereby the monoaminergic antidepressant comprises a compound from the group consisting of selective serotonin reuptake inhibitors (SSRI), selective serotonin and noradrenalin reuptake inhibitors (SNRI) selective noradrenaline and dopamine reuptake inhibitors, selective norepinephrine-dopamine reuptake inhibitors, monoamine oxidase inhibitors, tricyclic antidepressants, and other monoaminergic antidepressants, preferably the monoaminergic antidepressant is selected from the group consisting of venlafaxin, sertralin, mirtazapin, escitalopram, citalopram, fluoxetine, paroxetin, duloxetin, bupropion, amitriptylin, clomipramin, trimipramin, tranylcypromin.

26. Method according to any one of items 19 to 25, wherein the methylation status is determined using a technique selected from the group consisting of bisulfite sequencing, pyrosequencing, MALDI-TOF, methylation sensitive enzymatic digestion, and qMSP.

27. Method according to any one of items 19 to 26, wherein the steps are performed before administration of a monoaminergic antidepressant.

28. Method according to any one of items 19 to 27, whereby the sample is selected from the group consisting of blood, serum, plasma, saliva, sputum and cerebrospinal fluid.

29. Method according to any one of items 19 to 28, wherein the patient is suspected to have or is suffering from a disease selected from the group consisting of depression, major depressive disorder, mild depression, panic disorder, social anxiety disorder, social phobia, bulimia nervosa, obsessive-compulsive disorder, post-traumatic stress disorder, and generalized anxiety disorder.

30. Method according to any one of items 1 to 12 and 19 to 28 comprising administering a monoaminergic antidepressant to a patient predicted to respond to a monoaminergic antidepressant.

31. A method of treating a patient suffering from or suspected of suffering from a depression or a depression related disease with a monoaminergic antidepressant comprising the steps (a) and (b):
   (a) identifying a patient with normal methylation or hypermethylation of the BDNF-gene promoter; and
   (b) administering the monoaminergic antidepressant to the patient.

32. Monoaminergic antidepressant for use in treating a patient suffering from or suspected of suffering from a depression or a depression related disease, wherein said patient is to be identified as having a normal methylation or hypermethylation of the BDNF-gene promoter; and wherein the monoaminergic antidepressant is to be administered to said patient.

33. Method according to item 31 or monoaminergic antidepressant according to item 32, whereby said BDNF-gene promoter is BDNF-gene exon-IV promoter (SEQ ID NO. 1).

34. Method according to item 33 or monoaminergic antidepressant of item 33, whereby hypomethylation of the BDNF-gene exon-IV promoter at at least one of a CpG island selected from the group consisting of CpG−87, CpG−148, CpG−111, CpG+18, CpG−66, CpG−58, CpG−35, CpG−39, CpG−24, CpG−11, CpG+20, CpG+36, CpG+42, CpG+51, and CpG+54 is attributed to the non-response to a monoaminergic antidepressant of said patient, and normal methylation or hypermethylation at at least one of a CpG island selected from the group consisting of CpG−87, CpG−148, CpG−111, CpG+18, CpG−66, CpG−58, CpG−35, CpG−39, CpG−24, CpG−11, CpG+20, CpG+36, CpG+42, CpG+51, and CpG+54 is attributed to the response to a monoaminergic antidepressant of said patient; preferably hypomethylation at CpG−87 is attributed to the non-response to a monoaminergic antidepressant of said patient, and normal methylation or hypermethylation at CpG−87 is attributed to the response to a monoaminergic antidepressant of said patient.

35. Method according to any one of items 31, 33 and 34 or monoaminergic antidepressant according to any one of items 32 to 34, whereby a methylated C fraction of less than 0.05 is attributed to the non-response of said patient to a monoaminergic antidepressant, preferably a methylated C fraction of less than 0.04, more preferably a methylated C fraction of 0.03 or less is attributed to the non-response of said patient to a monoaminergic antidepressant.

36. Method according to any one of items 31 and 33 to 34 or monoaminergic antidepressant according to any one of items 32 to 35, whereby the monoaminergic antidepressant comprises a compound from the group consisting of selective serotonin reuptake inhibitors (SSRI), selective serotonin and noradrenalin reuptake inhibitors (SNRI) selective noradrenaline and dopamine reuptake inhibitors, selective norepinephrine-dopamine reuptake inhibitors, monoamine oxidase inhibitors, tricyclic antidepressants, and other monoaminergic antidepressants, preferably the monoaminergic antidepressant is selected from the group consisting of venlafaxin, sertralin, mirtazapin, escitalopram, citalopram, fluoxetine, paroxetin, duloxetin, bupropion, amitriptylin, clomipramin, trimipramin, tranylcypromin and agomelatine.

37. Method according to any one of items 31 and 33 to 36 or monoaminergic antidepressant according to any one of items 32 to 36, wherein the methylation status is determined using a technique selected from the group consisting of bisulfite sequencing, pyrosequencing, MALDI-TOF, methylation sensitive enzymatic digestion, and qMSP.
38. Method according to any one of items 31 and 33 to 37, wherein step (a) is performed before administration of a monoaminergic antidepressant.
39. Method according to any one of items 31 and 33 to 38 or monoaminergic antidepressant according to any one of items 32 to 38, wherein the methylation or hypermethylation of the BDNF-gene promoter is identified in a sample of the patient.
40. Method according to item 39 or monoaminergic antidepressant according to item 39, whereby the sample is selected from the group consisting of blood, serum, plasma, saliva, sputum and cerebrospinal fluid.
41. Method according to any one of items 31 and 33 to 40 or monoaminergic antidepressant according to any one of items 32 to 40, wherein said depression or depression related disease is a disease selected from the group consisting of depression, major depressive disorder, mild depression, panic disorder, social anxiety disorder, social phobia, bulimia nervosa, obsessive-compulsive disorder, post-traumatic stress disorder, and generalized anxiety disorder.

In more detail, the present invention relates to a method for predicting the non-response or response to (a) monoaminergic antidepressant(s) of a patient suffering from a disease to be treated with such a monoaminergic antidepressant, said method comprising the steps: (i) determining the DNA-methylation status of a brain-derived neurotrophic factor (BDNF)-gene promoter in a sample of said patient; (ii) attributing a hypomethylation of said BDNF-gene promoter to the non-response to a monoaminergic antidepressant of said patient; and (iii) attributing normal methylation or hypermethylation of said BDNF-gene promoter to the response to a monoaminergic antidepressant of said patient.

The present invention, accordingly provides for a method for stratifying patients or patient groups for the treatment with (a) monoaminergic antidepressant(s), said method comprising the steps of
i) determining the DNA-methylation status of a brain-derived neurotrophic factor (BDNF)-gene promoter in a sample of said patient;
ii) attributing a hypomethylation of said BDNF-gene promoter to the non-response to a monoaminergic antidepressant of said patient; and
iii) attributing normal methylation or hypermethylation of said BDNF-gene promoter to the response to (a) monoaminergic antidepressant(s) of said patient;
wherein hypomethylation of said BDNP-gene promoter indicates that the patient is not suitable for therapy with (a) monoaminergic antidepressant(s) and that the patient should be treated with an alternative therapy to monoaminergic antidepressants; and
wherein normal methylation or hypermethylation f said BDNF-gene promoter indicates that the patient is to be treated with (a) monoaminergic antidepressant(s).

An "alternative therapy" for patients suffering from (a) depression(s) or other disorders to be treated with a monoaminergic antidepressant and having a hypomethylation of the BDNF-gene promoter may comprise, but is not limited to, psychotherapy, neuromodulatory treatments or electroconvulsive therapy (ECT).

In context of the present invention the term "predicting" also means "assessing" and the term "determining" also means "measuring". Accordingly, one aspect of the invention relates to a method for assessing the non-response or response to a monoaminergic antidepressant of a patient to be treated with a monoaminergic antidepressant, said method comprising the steps:
i) (optionally, obtaining a sample from the patient), measuring the DNA-methylation status of a brain-derived neurotrophic factor (BDNF)-gene promoter in a sample of said patient;
ii) attributing a hypomethylation of said BDNF-gene promoter to the non-response to a monoaminergic antidepressant of said patient; and
iii) attributing normal methylation or hypermethylation of said BDNF-gene promoter to the response to a monoaminergic antidepressant of said patient.

Accordingly, the invention also relates to a method for predicting the non-response or response to a monoaminergic antidepressant of a patient to be treated with a monoaminergic antidepressant, said method comprising determining the DNA-methylation status of a brain-derived neurotrophic factor (BDNF)-gene promoter in a sample of said patient, whereby hypomethylation of said BDNF-gene promoter is indicative of the non-response to a monoaminergic antidepressant of said patient; and/or whereby normal methylation or hypermethylation of said BDNF-gene promoter is indicative of the response to a monoaminergic antidepressant of said patient.

In one embodiment of the invention said BDNF-gene promoter is BDNF-gene exon-IV promoter (SEQ ID NO. 1). It is envisaged that hypomethylation of the BDNF-gene exon-IV promoter at at least one of a CpG island selected from the group consisting of CpG−87, CpG−148, CpG−111, CpG+18, CpG−66, CpG−58, CpG−35, CpG−39, CpG−24, CpG−11, CpG+20, CpG+36, CpG+42, CpG+51, and CpG+54 is indicative of the non-response to a monoaminergic antidepressant of said patient, and normal methylation or hypermethylation at at least one of a CpG island selected from the group consisting of CpG−87, CpG−148, CpG−111, CpG+18, CpG−66, CpG−58, CpG−35, CpG−39, CpG−24, CpG−11, CpG+20, CpG+36, CpG+42, CpG+51, and CpG+54 is indicative of the response to a monoaminergic antidepressant of said patient; preferably hypomethylation at CpG−87 is indicative of the non-response to a monoaminergic antidepressant of said patient, and normal methylation or hypermethylation at CpG−87 is indicative of the response to a monoaminergic antidepressant of said patient.

In one embodiment of the invention, a methylated C fraction of less than 0.05 is indicative of the non-response of said patient to a monoaminergic antidepressant, preferably a methylated C fraction of less than 0.04, more preferably a methylated C fraction of 0.03 or less is indicative of the non-response of said patient to a monoaminergic antidepressant. The calculation of the methylated C fraction is well known in the art and described herein below.

The above described stratification method of the invention (i.e. the method for predicting the non-response or response to a monoaminergic antidepressant of a patient suffering from a disease to be treated with a monoaminergic antidepressant) may be performed by using at least one primer pair for amplifying a BDNF-gene promoter or a fragment thereof.

Accordingly, in one aspect the invention relates to a method for predicting the non-response or response to a monoaminergic antidepressant of a patient to be treated with a monoaminergic antidepressant, said method comprising the steps:
i) amplifying a BDNF-gene promoter or a fragment thereof by using at least one primer pair and determining the DNA-methylation status of the BDNF-gene promoter in a sample of said patient;
ii) attributing a hypomethylation of said BDNF-gene promoter to the non-response to a monoaminergic antidepressant of said patient; and
iii) attributing normal methylation or hypermethylation of said BDNF-gene promoter to the response to a monoaminergic antidepressant of said patient.

As mentioned above, in context of the invention the term "predicting" also means "assessing" and the term "determining" also means "measuring". Thus, the invention relates to a method for assessing the non-response or response to a monoaminergic antidepressant of a patient to be treated with a monoaminergic antidepressant, said method comprising the steps:
i) (optionally, obtaining a sample from the patient), amplifying a BDNF-gene promoter or a fragment thereof by using at least one primer pair and measuring the DNA-methylation status of the BDNF-gene promoter in a sample of said patient;
ii) attributing a hypomethylation of said BDNF-gene promoter to the non-response to a monoaminergic antidepressant of said patient; and
iii) attributing normal methylation or hypermethylation of said BDNF-gene promoter to the response to a monoaminergic antidepressant of said patient.

Thus, the invention is directed to a method for predicting the non-response or response to a monoaminergic antidepressant of a patient to be treated with a monoaminergic antidepressant comprising amplifying a BDNF-gene promoter or a fragment thereof by using at least one primer pair and determining the DNA-methylation status of the BDNF-gene promoter in a sample of said patient, whereby a hypomethylation of said BDNF-gene promoter is indicative of the non-response to a monoaminergic antidepressant of said patient; and/or whereby normal methylation or hypermethylation of said BDNF-gene promoter is indicative of the response to a monoaminergic antidepressant of said patient.

As mentioned above and explained herein, the present invention also relates to a method for stratifying patients or patient groups for the treatment with (a) monoaminergic antidepressant(s), said method comprising the steps of
i) determining the DNA-methylation status of a brain-derived neurotrophic factor (BDNF)-gene promoter in a sample of said patient;
ii) attributing a hypomethylation of said BDNF-gene promoter to the non-response to a monoaminergic antidepressant of said patient; and
iii) attributing normal methylation or hypermethylation of said BDNF-gene promoter to the response to (a) monoaminergic antidepressant(s) of said patient;
wherein hypomethylation of said BDNP-gene promoter indicates that the patient is not suitable for therapy with (a) monoaminergic antidepressant(s) and that the patient should be treated with an alternative therapy to monoaminergic antidepressants; and
wherein normal methylation or hypermethylation f said BDNF-gene promoter indicates that the patient is to be treated with (a) monoaminergic antidepressant(s).

When this stratification method is employed, the methylation status of said BDNF-gene promoter is assessed. Should hypomethylation of the BDNF-gene promoter be present in a sample of the patient to be treated, said patient is in need of an alternative therapy, i.e. a therapy that is not or not solely based on treatment with monoaminergic antidepressants. Such patients should be treated with an alternative therapy to monoaminergic antidepressants. Such alternative therapy/therapies may comprise, but are not limited to psychotherapy, electro convulsive therapy (ECT). Therefore, alternative therapies for patients with hypomethylation may comprise, but are not limited to, psychotherapy and intensive psychotherapy, such as cognitive behavioral therapy, interpersonal therapy, cognitive behavioral analysis system of psychotherapy, acceptance and commitment therapy, metacognitive therapy, dialectic behavioral therapy, psychoanalysis and focal psychodynamic therapy and neuromodulatory treatments, like electro-convulsive therapy, repetitive transcranial magnetic stimulation, deep brain stimulation, vagus nerve stimulation. Patients with hypomethylation may benefit from pharmacological treatment regimes developed for treatment resistant depression, such as combination of antidepressants, augmentation of antidepressive treatment with antipsychotics, lithium, stimulants (e.g. methylphenidate, amphetamine salts, modafinil), thyroid hormones (thyroxin), opioids or pindolole.

In contrast, should a patient's sample show normal or hypermethylated of the BDNF-gene promoter, said patient is to be treated with (a) monoaminergic antidepressant(s) or at least with a therapy that also comprises the (additional) use of (a) monoaminergic antidepressant(s). The basis of such a treatment should be the treatment with monoaminergic antidepressants in cases of patients with normal or hypermethylation.

In context of the invention, the at least one primer pair may be suitable for amplifying the BDNF-gene exon-IV promoter. It is prioritized that this at least one primer pair is suitable for amplifying a fragment of the BDNF-gene exon-IV promoter, wherein said fragment comprises at least a CpG island (e.g. the CpG island CpG–87). This primer pair for amplifying the BDNF-gene promoter or a fragment thereof may comprise at least one sequence as shown in SEQ ID NO. 1 or 2.

In one aspect of the present invention, this primer pair for amplifying the BDNF-gene promoter or a fragment thereof may comprise a sequence having at least 70% identity to SEQ ID NO. 1 or 2, preferably having at least 80% identity to SEQ ID NO. 1 or 2, even more preferably having at least 90% identity to SEQ ID NO. 1 or 2, and yet more preferably having at least 95% or 99% identity to SEQ ID NO. 1 or 2. In one embodiment of the invention, the primer pair for amplifying the BDNF-gene promoter or a fragment thereof has the sequence of SEQ ID NO. 1 and SEQ ID NO. 2.

As described herein, the above described stratification methods of the invention (e.g. the method for predicting the non-response or response to a monoaminergic antidepressant of a patient suffering from a disease to be treated with a monoaminergic antidepressant and/or the stratification method for susceptible patients/patient groups for monoaminergic antidepressants) may be performed by using means for determining the methylation status of DNA. The means for determining the methylation status of DNA can be, e.g., bisulfite, preferably sodium bisulfite. The determination whether a DNA is hyper-, hypo- or normally methylated is known in the art and also described and exemplified herein below. In addition, in accordance with the stratification methods of the present invention, control data may be used, wherein said control data determines whether the DNA of a BDNF-gene promoter is hypomethylated, normal methylated or hypermethylated.

In one embodiment, the invention relates to the above described stratification methods (i.e. the method for predicting the non-response or response to a monoaminergic antidepressant of a patient suffering from a disease to be treated with a monoaminergic antidepressant and/or the stratification for susceptible patients/patient groups for monoaminergic antidepressants) comprising administering a monoaminergic antidepressant to a patient predicted to respond to a monoaminergic antidepressant.

Accordingly, the invention provides a method of treating a patient suffering from or suspected of suffering from a depression or a depression related disease with a monoaminergic antidepressant comprising the steps (a) and (b):
(a) identifying a patient with normal methylation or hypermethylation of the BDNF-gene promoter; and
(b) administering the monoaminergic antidepressant to the patient.

Thus, the invention relates to a method of treating a patient with a monoaminergic antidepressant comprising the steps (a) and (b):
(a) predicting the non-response or response to a monoaminergic antidepressant of a patient suffering from a disease to be treated with a monoaminergic antidepressant comprising the steps:
  (i) determining the DNA-methylation status of a brain-derived neurotrophic factor (BDNF)-gene promoter in a sample of said patient;
  (ii) attributing a hypomethylation of said BDNF-gene promoter to the non-response to a monoaminergic antidepressant of said patient; and
  (iii) attributing normal methylation or hypermethylation of said BDNF-gene promoter to the response to a monoaminergic antidepressant of said patient; and
(b) administering the monoaminergic antidepressant to a patient that has been identified as responding to the monoaminergic antidepressant.

For patients having hypomethylation of the BDNF-gene promoter, alternative therapies, like psychotherapy, electro convulsive therapy (CET) should be employed as medical intervention of choice. Such patients are in need of particular intensive psychotherapy.

In the above described treatment method, step (a) may be performed before, during or after onset of treatment with the monoaminergic antidepressant. It is prioritized that step (a) is performed before administration of the monoaminergic antidepressant.

As described herein, in context of the methods of the invention, said depression or depression related disease may be a disease selected from the group consisting of depression, major depressive disorder, mild depression, panic disorder, social anxiety disorder, social phobia, bulimia nervosa, obsessive-compulsive disorder, post-traumatic stress disorder, and generalized anxiety disorder.

In accordance with the treatment method of the present invention, a monoaminergic antidepressant is administered to a patient in need of such a treatment, wherein the patient has been identified as responding to the treatment with a monoaminergic antidepressant by the method comprising the steps: (i) determining the DNA-methylation status of a brain-derived neurotrophic factor (BDNF)-gene promoter in a sample of said patient; (ii) attributing a hypomethylation of said BDNF-gene promoter to the non-response to a monoaminergic antidepressant of said patient; and (iii) attributing normal methylation or hypermethylation of said BDNF-gene promoter to the response to a monoaminergic antidepressant of said patient. Accordingly, in accordance with the treatment method of the invention, a monoaminergic antidepressant is administered to a patient whose BDNF-gene promoter is normal methylated or hypermethylated.

In a further aspect, the invention is directed to a monoaminergic antidepressant for use in treating a patient suffering from or suspected of suffering from a depression or a depression related disease, wherein said patient is to be identified as having a normal methylation or hypermethylation of the BDNF-gene promoter; and wherein the monoaminergic antidepressant is to be administered to said patient. Accordingly, the invention relates to a monoaminergic antidepressant for use in the treatment of a depression or a depression related disease, wherein said patient has a normal methylated or hypermethylated BDNF-gene promoter and the treatment comprises the step of determining whether or not the patient has a normal methylated or hypermethylated BDNF-gene promoter.

In accordance with the present invention, the monoaminergic antidepressant may be administered in a pharmaceutical composition. Such a pharmaceutical composition may routinely contain pharmaceutically acceptable concentrations of salt, buffering agents, preservatives, compatible carriers, and optionally other therapeutic agents. The pharmaceutical composition comprising the monoaminergic antidepressant can be administered by any conventional route. The administration may, for example, be oral, intravenous, intraperitoneal, intramuscular, intracavity, subcutaneous, or transdermal. A preferred route of administration is oral or via intravenous infusion. Techniques for preparing oral delivery systems containing monoaminergic antidepressant are well known to those of skill in the art. Generally, such systems should utilize components which will not significantly impair the biological properties of the monoaminergic antidepressant. Those of skill in the art can readily determine the various parameters and conditions for producing a medicament for oral administration of a monoaminergic antidepressant without resort to undue experimentation.

In a pharmaceutical composition at least one monoaminergic antidepressant may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The pharmaceutical composition may contain suitable buffering agents, e.g., acetic acid in a salt; citric acid in a salt; boric acid in a salt; and phosphoric acid in a salt. The pharmaceutical composition also may contain, optionally, suitable preservatives, e.g., benzalkonium chloride; chlorobutanol; or parabens.

In context of the present invention, a pharmaceutical composition comprising the monoaminergic antidepressant which is used in the foregoing methods preferably is sterile and contains an effective amount of monoaminergic antidepressant for producing the desired response in one or several unit(s) of weight or volume suitable for administration to a patient.

In accordance with the invention, the monoaminergic antidepressant may be administered in an effective amount.

An "effective amount" is that amount of a monoaminergic antidepressant that alone, or together with further doses, produces the desired response. In the case of treating a particular disease the desired response is inhibiting the progression of the disease. This may involve only slowing the progression of the disease temporarily, although more preferably, it involves halting the progression of the disease permanently. This can be monitored by routine diagnostic methods which are known in the art and also described herein.

Such effective amounts will depend, of course, on the particular condition being treated, the severity of the condition, the individual patient parameters including age, physical condition, size and weight, the duration of the treatment, the nature of concurrent therapy (if any), the specific route of administration and other factors within the knowledge and expertise of the health practitioner. These factors are well known to those of ordinary skill in the art and can be addressed with no more than routine experimentation. The effective dose may be, e.g., the maximum dose of the monoaminergic antidepressant, that is, the highest safe dose according to sound medical judgment.

The doses of monoaminergic antidepressant administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In context of the present invention monoaminergic antidepressants may be administered in doses between 0.1 mg per day (mg/d) and 5000 mg/d, and preferably between 1 mg/d and 500 mg/d. In context of the present invention, the following doses may be used: escitalopram (e.g. 10 to 20 mg/d), sertraline (e.g. 50 to 150 mg/d), fluoxetine (e.g. 20 mg/d), venlafaxine (e.g. 150 to 375 mg/d), duloxetine (e.g. 90 to 120 mg/d), mirtazapine (e.g. 30 to 45 mg/d), tranylcypromine (e.g. 30 mg/d), amitriptyline (e.g. 225 mg/d), clomipramine (e.g. 150 mg/d), trimipramine (e.g. 100 mg/d) or agomelatine (e.g. 25 to 50 mg/d).

During treatment of the patients severity of the disease to be treated (e.g. the depression) may be assessed. For example the severity of a depression may be assessed (e.g. weekly) by the 21-item Hamilton Depression Rating Scale (HAMD-21).

Other protocols for the administration of monoaminergic antidepressants will be known to one of ordinary skill in the art, in which the dose amount, schedule of administration, mode of administration and the like vary from the foregoing. Administration of monoaminergic antidepressants to mammals other than humans, (e.g. for testing purposes or veterinary therapeutic purposes), may be carried out under substantially the same conditions as described above.

The pharmaceutical composition comprising at least one monoaminergic antidepressant may conveniently be presented in unit dosage form and may be prepared by any of the methods well-known in the art of pharmacy. The method may include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Pharmaceutical compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Pharmaceutical compositions suitable for parenteral administration may comprise a sterile aqueous or non-aqueous preparation of at least one monoaminergic antidepressant, which may be isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent. Among the acceptable vehicles and solvents that may be employed are water, Ringer's solution, and isotonic sodium chloride solution. In addition, sterile, fixed oils are conventionally employed as a solvent or suspending medium. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

The stratification method of the invention, (i.e. the method for predicting the non-response or response to a monoaminergic antidepressant of a patient suffering from a disease to be treated with a monoaminergic antidepressant) may be an ex vivo or in vitro method.

The skilled artisan is aware of diseases which are to be treated with monoaminergic antidepressants. The mechanism of monoaminergic antidepressants is known by those of skills in the art. Basically, all monoaminergic antidepressants increase the level of the neurotransmitters serotonin, dopamine and/or norepinephrine in the synaptic cleft, either by inhibition of the molecules facilitating the reuptake of the transmitter into the presynaptic neuron or by inhibiting the enzymes responsible for the degradation of said neurotransmitters, or by increasing the presynaptic release of the neurotransmitter by inhibition of presynaptic receptors. Diseases which are treated with a monoaminergic antidepressant are hence clear and known to those skilled in the art. A summary may be found in Benkert, Hippius. Kompendium der Psychiatrischen Pharmakotherapie, 8. Auflage 2010, Springer Medizin Verlag Heidelberg; Kapitel 1: Antidepressiva; starting page 1.

"Patients" in the meaning of the invention are understood to be all persons and animals which are suspected to have or has a disease which can be treated with a monoaminergic antidepressant. In the meaning of the invention, any sample collected from cells, tissues, organs, organisms or the like can be a sample of a patient to be diagnosed. In a preferred embodiment, the patient according to the invention is a human individual suspected to have or having a disease which can be treated with a monoaminergic antidepressant. Said patient may be a human individual suspected to have or having/suffering from a depression or a depression related disease.

In one embodiment of the present invention the patient is suffering from a depression or a depression related disease. Hence, the present invention also relates to a method for predicting the non-response or response to a monoaminergic antidepressant of a patient suffering from depression or a depression related disease comprising the steps: (i) determining the DNA-methylation status of a brain-derived neurotrophic factor (BDNF)-gene promoter in a sample of said patient; (ii) attributing a hypomethylation of said BDNF-gene promoter to the non-response to a monoaminergic antidepressant of said patient; and (iii) attributing normal methylation or hypermethylation of said BDNF-gene promoter to the response to a monoaminergic antidepressant of said patient.

The term "depression" in context with the present invention refers a state of mental disorder, characterized by sadness, loss of interest or pleasure, feelings of guilt or low self-worth, disturbed sleep or appetite, low energy and poor concentration. Depressed people may feel sad, anxious, empty, hopeless, worried, helpless, worthless, guilty, irritable, or restless. They may lose interest in activities that once were pleasurable; experience loss of appetite or overeating, have problems concentrating, remembering details, or making decisions; and may contemplate or attempt suicide. Insomnia, excessive sleeping, fatigue, loss of energy, aches, pains or digestive problems that are resistant to treatment may be present. The skilled artisan is able to determine whether a patient is suffering from a depression. He may perform a full patient medical history, physical assessment, and thorough evaluation of symptoms to determine the cause of the depression. Standardized questionnaires can be helpful such as the Hamilton Rating Scale for Depression (Zimmerman M, Chelminski I, Posternak M (2004 September). "A review of studies of the Hamilton depression rating scale in healthy controls: implications for the definition of remission in treatment studies of depression.". *J Nerv Ment Dis* 192 (9): 595-601). and the Beck Depression Inventory (McPherson A, Martin C R (2010 February). "A narrative review of the Beck Depression Inventory (BDI) and implications for its use in an alcohol-dependent population". *J Psychiatr Ment Health Nurs* 17 (1): 19-30). Generally a medical examination and selected investigations are performed to rule out other causes of symptoms. These include blood tests measuring TSH and thyroxine to exclude hypothyroidism; basic electrolytes and serum calcium to rule out a metabolic disturbance; and a full blood count including ESR to rule out a systemic infection or chronic disease. Adverse affective reactions to medications or alcohol misuse are often ruled out, as well. Testosterone levels may be evaluated to diagnose hypogonadism, a cause of depression in men (Orengo C, Fullerton G, Tan R. Male depression: A review of gender concerns and testosterone therapy. *Geriatrics*. 2004; 59(10):24-30). Subjective cognitive complaints appear in older depressed people, but they can also be indicative of the onset of a dementing disorder, such as Alzheimer's disease (Reid L M, Maclullich A M. Subjective memory complaints and cognitive impairment in older people. *Dementia and geriatric cognitive disorders*. 2006; 22(5-6):471-485; and Katz I R. Diagnosis and treatment of depression in patients with Alzheimer's disease and other dementias. *The Journal of clinical psychiatry*. 1998; 59 Suppl 9:38-44). Cognitive testing and brain imaging can help distinguish depression from dementia (Wright S L, Persad C. Distinguishing between depression and dementia in older persons: Neuropsychological and neuropathological correlates. *Journal of geriatric psychiatry and neurology*. 2007; 20(4):189-98). A computer tomography scan can exclude brain pathology in those with psychotic, rapid-onset or otherwise unusual symptoms; see, e.g. Sadock, Virginia A.; Sadock, Benjamin J.; Kaplan, Harold I. *Kaplan & Sadock's synopsis of psychiatry: behavioral sciences/clinical psychiatry*. Philadelphia: Lippincott Williams & Wilkins; 2003, page 108) No biological tests confirm major depression (Sadock, Virginia A.; Sadock, Benjamin J.; Kaplan, Harold I. *Kaplan & Sadock's synopsis of psychiatry: behavioral sciences/clinical psychiatry*. Philadelphia: Lippincott Williams & Wilkins; 2003, page 260). Investigations are not generally repeated for a subsequent episode unless there is a medical indication. The term depression in connection with the present invention comprises all kind of depression. However, in a preferred embodiment depression is selected from the group consisting of depression, major depressive disorder, mild depression.

The rating for major depressive disorder and mild depression can be performed by those of ordinary skills in the art, e.g. using the standards of the Hamilton Depression Rating Scale (HAMD-21).

The term "major depressive disorder" refers to a severe course of depression. A severe course is defined by the Diagnostic and Statistical Manual of Mental Disorders of the American Psychiatric Association (American Psychiatric Association: Diagnostic and Statistical Manual of Mental disorders. DSM-IV-TR. 4th Edition, Text Revision. American Psychiatric Association, Washington D.C. 2000, ISBN 0-89042-024-6) as follows:

A. Five (or more) of the following symptoms have been present during the same 2-week period and represent a change from previous functioning; at least one of the symptoms is either (1) depressed mood or (2) loss of interest or pleasure.

1. Depressed mood most of the day, nearly every day, as indicated by either subjective report (e.g., feels sad or empty) or observation made by others (e.g., appears tearful).
2. Markedly diminished interest or pleasure in all, or almost all, activities most of the day, nearly every day (as indicated by either subjective account or observation made by others)
3. Significant weight loss when not dieting or weight gain (e.g., a change of more than 5% of body weight in a month), or decrease or increase in appetite nearly every day.
4. Insomnia or hypersomnia nearly every day
5. Psychomotor agitation or retardation nearly every day (observable by others, not merely subjective feelings of restlessness or being slowed down)
6. Fatigue or loss of energy nearly every day
7. Feelings of worthlessness or excessive or inappropriate guilt (which may be delusional) nearly every day (not merely self-reproach or guilt about being sick)
8. Diminished ability to think or concentrate, or indecisiveness, nearly every day (either by subjective account or as observed by others)
9. Recurrent thoughts of death (not just fear of dying), recurrent suicidal ideation without a specific plan, or a suicide attempt or a specific plan for committing suicide B. The symptoms do not meet criteria for a Mixed Episode.
C. The symptoms cause clinically significant distress or impairment in social, occupational, or other important areas of functioning.
D. The symptoms are not due to the direct physiological effects of a substance (e.g., a drug of abuse, a medication) or a general medical condition (e.g., hypothyroidism).
E. The symptoms are not better accounted for by Bereavement, i.e., after the loss of a loved one, the symptoms persist for longer than 2 months or are characterized by marked functional impairment, morbid preoccupation with worthlessness, suicidal ideation, psychotic symptoms, or psychomotor retardation.

The term "mild depression" refers to a mild course of depression. Mild course of depression means that two or more symptoms of depression (DSM-IV criterion A: 1-9) are present but either less than 5 or the other criteria of a major depressive disorder as outlined above are not fulfilled The term "depression related disease" refers to diseases which can be treated with monoaminergic antidepressants.

As outlined above, such diseases are known by those skilled in the art. However, in a preferred embodiment the patient is suffering from a depression related disease selected from the group consisting of panic disorder, social anxiety disorder, social phobia, bulimia nervosa, obsessive-compulsive disorder, post-traumatic stress disorder, and generalized anxiety disorder. All these disorders are known by those of ordinary skills in the art.

As outlined above, the skilled artisan knows that for the diagnosis of a depression different tests may be necessary, including tests for excluding the patient suffering from another disease or the patient being in certain states. Hence, in one embodiment the patient is diagnosed for the non-presence of a disease or state selected from the group consisting of lifetime diagnosis of dementia, schizophrenia, schizoaffective disorder, current diagnosis of alcohol dependency requiring acute detoxification, Parkinson's disease, multiple sclerosis, pregnancy, breast feeding, and cognitive impairment.

The term "response" in connection with the present invention refers to an at least partial reduction of symptoms of the disease the patient is suffering from and which is to be treated with a monoaminergic antidepressant in a patient during or after the treatment with monoaminergic antidepressants, e.g. symptoms of depression or the depression related disease.

The term "non-response" within the meaning of the present invention refers to the absence of reduction of symptoms of a disease, e.g. depression or a depression related disease or the presence of an increase of symptoms of depression or depression related disease in a patient during or after the treatment with monoaminergic antidepressants.

Remission is the state of absence of disease activity in patients known to have a chronic illness that cannot be cured. In context with the present invention remission has to be understood as comprised in the term "response". Remission has to be seen as the most possible response leading to the complete absence of the disease activity and symptoms. "Non-remission" means that the disease activities and symptoms do not disappear completely. However, as the method according to the present invention is able to predict both, non-response and non-remission, the methods, kits and uses disclosed herein are to be understood as being methods for predicting non-remission or non-response.

The term "methylation status" refers to the presence or absence of 5-methylcytosine ("5-mCyt") at one or a plurality of CpG dinucleotides within a DNA sequence. The terms methylated cytosine, 5-mCyt, and 5-methylcytosine are used interchangeably herein.

The BDNF-locus is known to those skilled in the art (GeneID No. 612). As outlined above, it is consisting of 11 exons and codes for at least 15 different transcripts having starting points before different 5'-exons. Known promoters are disclosed in Pruunsild et al. (2007), supra, which is incorporated herein by reference.

The inventors astonishingly found that the promoter region of BDNF-gene exon-IV is sufficient for the predictive method according to the present invention. This BDNF-gene exon-IV promoter comprises a CpG island that spans from CpG−148 to CpG+54. Hence, in one embodiment of the present invention the methylation status of the BDNF-gene exon IV promoter is determined. The BDNF-gene exon-IV promoter spans from 27723103 to 27723380 (rev strand) of Chromosome 11 of the human genome (NCBI NC_000011.9). Hence, in one embodiment of the present invention the methylation status of a BDNF-gene promoter is determined, wherein said BDNF-gene promoter comprises at least the sequence of SEQ ID NO. 1, or a sequence having at least 70% identity thereto, preferably at least 80% identity to SEQ ID NO. 1, even more preferably at least 90% identity to SEQ ID NO. 1, yet more preferably at least 95% identity to SEQ ID NO. 1. In a further preferred embodiment said BDNF-gene promoter comprises a sequence having at least 99% identity to SEQ ID NO. 1. Hence, in one embodiment of the present invention said (BDNF)-gene promoter is the BDNF-gene exon-IV promoter (SEQ ID NO. 1). As being apparent to those skilled in the art, sequences in the genome often comprise polymorphisms, i.e. varying sequences between different individuals. Therefore, in one embodiment the BDNF-gene exon-IV promoter according to the present invention has a sequence having at least 70% identity to SEQ ID NO. 1, preferably at least 80% identity to SEQ ID NO. 1, even more preferably at least 90% identity to SEQ ID NO. 1, yet more preferably at least 95% identity to SEQ ID NO. 1. In a further preferred embodiment the BDNF-gene exon-IV promoter has at least 99% identity to SEQ ID NO. 1.

The determination of percent identity between two sequences is accomplished using the mathematical algorithm of Karlin and Altschul (1993) Proc. Natl. Acad. Sci. USA 90: 5873-5877. Such an algorithm is incorporated into the BLASTN and BLASTP programs of Altschul et al. (1990) J. Mol. Biol. 215: 403-410. BLAST nucleotide searches are performed with the BLASTN program, score=100, word length=12, to obtain nucleotide sequences homologous to the EPO variant polypeptide encoding nucleic acids. BLAST protein searches are performed with the BLASTP program, score=50, word length=3, to obtain amino acid sequences homologous to the EPO variant polypeptide, respectively. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used.

The inventors furthermore found that several CpG dinucleotides in the BDNF-gene exon-IV promoter are well suited for prediction with the method according to the present invention. In the following table an overview of preferred CpG dinucleotides is given. The number in the name of the CpG dinucleotides refers to the position of the CpG dinucleotide relative to the first nucleotide of exon IV of the BDNF-gene, for example CpG dinucleotide CpG−87 is positioned 87 nucleotides upstream of the first nucleotide of BDNF exon-IV. The position of the CpG dinucleotide in SEQ ID NO. 1 is given in the middle column. The position on chromosome 11 (reverse Strand) is given in the right column according to NCBI-nomenclature (NCBI NC_000011.9).

TABLE 1 preferred CpG dinucleotides of the present invention

| Name | Position in SEQ ID NO. 1 | Position on chromosome 11 (rev-strand) |
|---|---|---|
| CpG-87 | 114 | 27723267 |
| CpG-148 | 53 | 27723328 |
| CpG-111 | 90 | 27723291 |
| CpG + 18 | 218 | 27723162 |
| CpG-66 | 135 | 27723246 |
| CpG-58 | 143 | 27723238 |
| CpG-39 | 162 | 27723219 |

TABLE 1-continued preferred CpG dinucleotides of the present invention

| Name | Position in SEQ ID NO. 1 | Position on chromosome 11 (rev-strand) |
|---|---|---|
| CpG-35 | 166 | 27723215 |
| CpG-24 | 175 | 27723204 |
| CpG-11 | 188 | 27723191 |
| CpG + 20 | 220 | 27723160 |
| CpG + 36 | 236 | 27723144 |
| CpG + 42 | 242 | 27723138 |
| CpG + 51 | 251 | 27723129 |
| CpG + 54 | 254 | 27723126 |

In a preferred embodiment of the present invention hypomethylation of the BDNF-gene exon-IV promoter at at least one of a CpG dinucleotides selected from the group consisting of CpG-87, CpG-148, CpG-111, CpG+18, CpG-66, CpG-58, CpG-35, CpG-39, CpG-24, CpG-11, CpG+20, CpG+36, CpG+42, CpG+51, and CpG+54 is attributed to the non-response to a monoaminergic antidepressant of said patient, and normal methylation or hypermethylation at at least one of a CpG dinucleotides selected from the group consisting of -87, CpG-148, CpG-111, CpG+18, CpG-66, CpG-58, CpG-35, CpG-39, CpG-24, CpG-11, CpG+20, CpG+36, CpG+42, CpG+51, and CpG+ 54 is attributed to the response to a monoaminergic antidepressant of said patient.

It has been found that the methylation status at CpG dinucleotide CpG-87 is sufficient for the predictive method according to the present invention. Hence, in a further preferred embodiment of the present invention hypomethylation at CpG-87 is attributed to the non-response to a monoaminergic antidepressant of said patient, and normal methylation or hypermethylation at CpG-87 is attributed to the response to a monoaminergic antidepressant of said patient.

The term "hypermethylation" refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

The term "hypomethylation" refers to the average methylation state corresponding to a decreased presence of 5-mCyto at one or a plurality of CpG dinucleotides within a DNA sequence of a test DNA sample, relative to the amount of 5-mCytosine found at corresponding CpG dinucleotides within a normal control DNA sample.

The term "normal methylation" refers to the average methylation state corresponding to a equal or comparable presence of 5-mCytosine at one or a plurality of CpG dinucleotides within a DNA sequence of a test DNA sample, relative to the amount of 5-mCytosine found at corresponding CpG dinucleotides within a normal control DNA sample.

The skilled person is readily in the position to determine whether a DNA is hyper-, hypo- or normally methylated. For example the determined relative amount of methylated cytosines at a specific CpG dinucleotide or island from a patient may be compared to the relative amount of a control person or a control group of persons known to respond to monoaminergic antidepressants. In the case where the relative amount of methylated C in the sample of the patient to be treated at the specific position, e.g. at CpG-87, is lower than in the control person or control group this will be attributed to the non-response to a monoaminergic antidepressant in the method according to the present invention. Hence, in one embodiment of the invention the method comprises the step of comparing the determined methylation status of said BDNF-gene promoter of said patient to the methylation status of said BDNF-gene promoter in a control. The skilled artisan in this case will acknowledge that the term "hypermethylated" refers to a smaller methylated C fraction in the sample of said patient than in the control group. The term "hypermethylated" instead refers to a higher methylated C fraction in the sample of said patient than in the control group. The term "normal methylation" in this case refers to an equal or comparable methylated C fraction in the sample of said patient to that in the control group. It will be readily recognized by those of ordinary skills in the art that the methylation status of the BDNF-gene promoter of said control may be a data indicating the average methylated C fraction of said BDNF-gene promoter persons.

The determination of the methylation status can be performed by different assays as outlined herein and known in the art. However, in a preferred embodiment the methylation status is determined by contacting the DNA from said sample with bisulfite or a salt thereof, and sequencing said BDNF-gene promoter or fragments thereof, and evaluating the obtained sequence for bisulfite converted DNA, preferably using the ESME algorithm ([Lewin J, Schmitt A O, Adorjan P, Hildmann T, Piepenbrock C. Quantitative DNA methylation analysis based on four-dye trace data from direct sequencing of PCR amplificates. *Bioinformatics* 2004; 20(17):3005-3012).

The term "ESME" refers to a particularly preferred software program that considers or accounts for the unequal distribution of bases in bisulfite converted DNA and normalizes the sequence traces (electropherograms) to allow for quantitation of methylation signals within the sequence traces. Additionally, it calculates a bisulfite conversion rate, by comparing signal intensities of thymines at specific positions, based on the information about the corresponding untreated DNA sequence.

The methylation status as obtained by the methods or the use of the methods according to the present invention may be analyzed in a number of fashions well known to a person skilled in the art. For example, each assay result obtained may be compared to a "normal" value, such as the sample from said control patient, or a value indicating a particular disease or outcome. A particular diagnosis/prognosis may depend upon the comparison of each assay result to such a value, which may be referred to as a diagnostic or prognostic "threshold". In certain embodiments, assays for one or more diagnostic or prognostic indicators are correlated to a condition or disease by merely the presence or absence of the indicator(s) in the assay. For example, an assay can be designed so that a positive signal only occurs above a particular threshold concentration of interest, and below which concentration the assay provides no signal above background.

The sensitivity and specificity of a prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy) and "disease" populations. For any particular marker, a distribution of marker levels for subjects with and without a disease will likely overlap. Under such conditions, a test does not absolutely distinguish response from non-response with 100% accuracy, and the area of overlap indicates where the test cannot distinguish response from non-response. A threshold is selected, above which (or below which, depending on how a marker changes with the response) the test is considered to be a response and below which the test is considered to be non-response. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "response" samples might be ranked according to degree (e.g. 1=low, 2=normal, and 3=high). This ranking can be correlated to results in the "response" or "normal" population, and a ROC curve can be created. These methods are well known in the art; see, e.g., Hanley et al. 1982. Radiology 143: 29-36.

Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

In certain embodiments, particular thresholds for one or more markers in a panel are not relied upon to determine if a profile of the methylation statuses obtained from a subject are indicative of a particular prediction. Rather, the present invention may utilize an evaluation of a panel "profile" as a unitary whole. A particular "fingerprint" pattern of changes in such a panel of methylation statuses may, in effect, act as a specific predictive indicator. As discussed herein, that pattern of changes may be obtained from a single sample, or from temporal changes in one or more members of the panel (or a panel response value). A panel herein refers to a set of methylation statuses, e.g. of different CpG-dinucleotides.

As described herein after, a panel response value is preferably determined by plotting ROC curves for the sensitivity (i.e. true positives) of a particular panel of markers versus 1-(specificity) (i.e. false positives) for the panel at various cut-offs. In these methods, a profile of methylation measurements from a subject is considered together to provide a global probability (expressed either as a numeric score or as a percentage risk) of a prediction of response. In such embodiments, a decrease in a certain subset of methylation may be sufficient to indicate non-response in one patient, while a decrease in a different subset of markers may be sufficient to indicate the same or a different prediction in another patient. Weighting factors may also be applied to one or more markers in a panel, e.g. CpG dinucleotides, for example, when a CpG dinucleotide is of particularly high utility in identifying response or non-response, it may be weighted so that at a given methylation status alone is sufficient to response or non-response.

Likewise, a weighting factor may provide that no given level of a particular marker is sufficient to signal a positive result, but only signals a result when another marker also contributes to the analysis.

In certain embodiments, methylation statuses or panel of methylation statuses are selected to exhibit at least about 70% sensitivity, more preferably at least about 80% sensitivity, even more preferably at least about 85% sensitivity, still more preferably at least about 90% sensitivity, and most preferably at least about 95% sensitivity, combined with at least about 70% specificity, more preferably at least about 80% specificity, even more preferably at least about 85% specificity, still more preferably at least about 90% specificity, and most preferably at least about 95% specificity. In particularly preferred embodiments, both the sensitivity and specificity are at least about 75%, more preferably at least about 80%, even more preferably at least about 85%, still more preferably at least about 90%, and most preferably at least about 95%. The term "about" in this context refers to +/−5% of a given measurement.

A positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "non-response" and "response" groups; a value greater than 1 indicates that a positive result is more likely in the non-response group; and a value less than 1 indicates that a positive result is more likely in the response group. In the case of a negative likelihood ratio, a value of 1 indicates that a negative result is equally likely among subjects in both the "non-response" and "response" groups; a value greater than 1 indicates that a negative result is more likely in the test group; and a value less than 1 indicates that a negative result is more likely in the response group. In certain preferred embodiments, methylation statuses and panels of methylation statuses are preferably selected to exhibit a positive or negative likelihood ratio of at least about 1.5 or more or about 0.67 or less, more preferably at least about 2 or more or about 0.5 or less, still more preferably at least about 5 or more or about 0.2 or less, even more preferably at least about 10 or more or about 0.1 or less, and most preferably at least about 20 or more or about 0.05 or less. The term "about" in this context refers to +/−5% of a given measurement.

In the case of an odds ratio, a value of 1 indicates that a positive result is equally likely among subjects in both the "non-response" and "response" groups; a value greater than 1 indicates that a positive result is more likely in the non-response group; and a value less than 1 indicates that a positive result is more likely in the response group. In certain preferred embodiments, markers and/or marker panels are preferably selected to exhibit an odds ratio of at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less. The term "about" in this context refers to +/−5% of a given measurement, i.e. in on embodiment at least 12 or more or about 0.8 or less.

The skilled artisan will understand that associating predictive indicator, with a response or non-response. For example, a methylation status of less than X may signal that a patient is more likely to non-respond to a monoaminergic antidepressant than patients with a methylation status higher than or equal to X, as determined by a level of statistical significance. Additionally, a change in methylation from baseline levels may be reflective of patient prognosis, and the degree of change in marker level may be related to the severity response. Statistical significance is often determined by comparing two or more populations, and determining a confidence interval and/or a p value. See, e.g., Dowdy and Wearden, Statistics for Research, John Wiley &

Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

Even though the skilled person is able to determine suited thresholds for the predictive method according to the present invention as outlined above, the inventors found that specific thresholds are predictive for the response or non-response according to the present invention. Hence, in a preferred embodiment of the present invention a methylated C fraction of less than 0.05 is attributed to the non-response of said patient to a monoaminergic antidepressant, preferably a methylated C fraction of less than 0.04, more preferably a methylated C fraction of 0.03 or less is attributed to the non-response of said patient to a monoaminergic antidepressant. Accordingly, in a further embodiment of the invention a methylated C fraction of more than 0.03 is attributed to the response of said patient to a monoaminergic antidepressant, preferably a methylated C fraction of more than 0.04, more preferably a methylated C fraction of 0.05 or more is attributed to the response of said patient to a monoaminergic antidepressant.

CpG−87

In a further preferred embodiment of the present invention a methylated C fraction of less than 0.05 at CpG−87 is attributed to the non-response of said patient to a monoaminergic antidepressant, preferably a methylated C fraction of less than 0.04 at CpG−87, more preferably a methylated C fraction of 0.03 at CpG−87 or less is attributed to the non-response of said patient to a monoaminergic antidepressant. Accordingly, in a further embodiment of the invention a methylated C fraction of more than 0.03 at CpG−87 is attributed to the response of said patient to a monoaminergic antidepressant, preferably a methylated C fraction of more than 0.04 at CpG−87, more preferably a methylated C fraction of 0.05 or more at CpG−87 is attributed to the response of said patient to a monoaminergic antidepressant. In a certain preferred embodiment of the present invention a methylated C fraction of less than 0.05 at CpG−87 is attributed to the non-response of said patient to a monoaminergic antidepressant, and a methylated C fraction of 0.05 or more at CpG−87 is attributed to the response of said patient to a monoaminergic antidepressant.

The thresholds given above are thresholds determined by the inventors and have been exemplified for CpG−87 herein below. However, for different CpG dinucleotides different thresholds may be given for the method according to the present invention and can be determined by statistical methods as outlined herein above.

However, for other than CpG−87 other preferred thresholds are disclosed in the following:

CpG−148

In one embodiment of the present invention a methylated C fraction of less than 0.10 at CpG−148 is attributed to the non-response of said patient to a monoaminergic antidepressant, preferably a methylated C fraction of less than 0.09 at CpG−148, more preferably a methylated C fraction of 0.08 at CpG−148 or less is attributed to the non-response of said patient to a monoaminergic antidepressant. Accordingly, in a further embodiment of the invention a methylated C fraction of more than 0.08 at CpG−148 is attributed to the response of said patient to a monoaminergic antidepressant, preferably a methylated C fraction of more than 0.09 at CpG−148, more preferably a methylated C fraction of 0.10 or more at CpG−148 is attributed to the response of said patient to a monoaminergic antidepressant.

CpG−111

In one embodiment of the present invention a methylated C fraction of less than 0.12 at CpG−111 is attributed to the non-response of said patient to a monoaminergic antidepressant, preferably a methylated C fraction of less than 0.11 at CpG−111, more preferably a methylated C fraction of 0.10 at CpG−111 or less is attributed to the non-response of said patient to a monoaminergic antidepressant. Accordingly, in a further embodiment of the invention a methylated C fraction of more than 0.10 at CpG−111 is attributed to the response of said patient to a monoaminergic antidepressant, preferably a methylated C fraction of more than 0.11 at CpG−111, more preferably a methylated C fraction of 0.12 or more at CpG−111 is attributed to the response of said patient to a monoaminergic antidepressant.

CpG+18

In one embodiment of the present invention a methylated C fraction of less than 0.03 at CpG+18 is attributed to the non-response of said patient to a monoaminergic antidepressant, preferably a methylated C fraction of less than 0.02 at CpG+18, more preferably a methylated C fraction of 0.01 at CpG+18 or less is attributed to the non-response of said patient to a monoaminergic antidepressant. Accordingly, in a further embodiment of the invention a methylated C fraction of more than 0.01 at CpG+18 is attributed to the response of said patient to a monoaminergic antidepressant, preferably a methylated C fraction of more than 0.02 at CpG+18, more preferably a methylated C fraction of 0.03 or more at CpG+18 is attributed to the response of said patient to a monoaminergic antidepressant.

CpG−66

In one embodiment of the present invention a methylated C fraction of less than 0.05 at CpG−66 is attributed to the non-response of said patient to a monoaminergic antidepressant, preferably a methylated C fraction of less than 0.04 at CpG−66, more preferably a methylated C fraction of 0.03 at CpG−66 or less is attributed to the non-response of said patient to a monoaminergic antidepressant. Accordingly, in a further embodiment of the invention a methylated C fraction of more than 0.03 at CpG−66 is attributed to the response of said patient to a monoaminergic antidepressant, preferably a methylated C fraction of more than 0.04 at CpG−66, more preferably a methylated C fraction of 0.05 or more at CpG−66 is attributed to the response of said patient to a monoaminergic antidepressant.

CpG−58

In one embodiment of the present invention a methylated C fraction of less than 0.12 at CpG−58 is attributed to the non-response of said patient to a monoaminergic antidepressant, preferably a methylated C fraction of less than 0.11 at CpG−58, more preferably a methylated C fraction of 0.10 at CpG−58 or less is attributed to the non-response of said patient to a monoaminergic antidepressant. Accordingly, in a further embodiment of the invention a methylated C fraction of more than 0.10 at CpG−58 is attributed to the response of said patient to a monoaminergic antidepressant, preferably a methylated C fraction of more than 0.11 at CpG−58, more preferably a methylated C fraction of 0.12 or more at CpG−58 is attributed to the response of said patient to a monoaminergic antidepressant.

CpG−35

In one embodiment of the present invention a methylated C fraction of less than 0.04 at CpG−35 is attributed to the non-response of said patient to a monoaminergic antidepressant, preferably a methylated C fraction of less than 0.03 at CpG−35, more preferably a methylated C fraction of 0.025 at CpG−35 or less is attributed to the non-response of said patient to a monoaminergic antidepressant. Accordingly, in a further embodiment of the invention a methylated C fraction of more than 0.025 at CpG−35 is attributed to the response of said patient to a monoaminergic antidepressant, preferably a methylated C fraction of more than 0.03 at CpG−35, more preferably a methylated C fraction of 0.04 or more at CpG−35 is attributed to the response of said patient to a monoaminergic antidepressant.

CpG−39

In one embodiment of the present invention a methylated C fraction of less than 0.05 at CpG−39 is attributed to the non-response of said patient to a monoaminergic antidepressant, preferably a methylated C fraction of less than 0.045 at CpG−39, more preferably a methylated C fraction of 0.04 at CpG−39 or less is attributed to the non-response of said patient to a monoaminergic antidepressant. Accordingly, in a further embodiment of the invention a methylated C fraction of more than 0.04 at CpG−39 is attributed to the response of said patient to a monoaminergic antidepressant, preferably a methylated C fraction of more than 0.045 at CpG−39, more preferably a methylated C fraction of 0.05 or more at CpG−39 is attributed to the response of said patient to a monoaminergic antidepressant.

CpG−24

In one embodiment of the present invention a methylated C fraction of less than 0.02 at CpG−24 is attributed to the non-response of said patient to a monoaminergic antidepressant, preferably a methylated C fraction of less than 0.015 at CpG−24, more preferably a methylated C fraction of 0.01 at CpG−24 or less is attributed to the non-response of said patient to a monoaminergic antidepressant. Accordingly, in a further embodiment of the invention a methylated C fraction of more than 0.01 at CpG−24 is attributed to the response of said patient to a monoaminergic antidepressant, preferably a methylated C fraction of more than 0.015 at CpG−24, more preferably a methylated C fraction of 0.02 or more at CpG−24 is attributed to the response of said patient to a monoaminergic antidepressant.

CpG−11

In one embodiment of the present invention a methylated C fraction of less than 0.02 at CpG−11 is attributed to the non-response of said patient to a monoaminergic antidepressant, preferably a methylated C fraction of less than 0.015 at CpG−11, more preferably a methylated C fraction of 0.01 at CpG−11 or less is attributed to the non-response of said patient to a monoaminergic antidepressant. Accordingly, in a further embodiment of the invention a methylated C fraction of more than 0.01 at CpG−11 is attributed to the response of said patient to a monoaminergic antidepressant, preferably a methylated C fraction of more than 0.015 at CpG−11, more preferably a methylated C fraction of 0.02 or more at CpG−11 is attributed to the response of said patient to a monoaminergic antidepressant.

CpG+20

In one embodiment of the present invention a methylated C fraction of less than 0.02 at CpG+20 is attributed to the non-response of said patient to a monoaminergic antidepressant, preferably a methylated C fraction of less than 0.015 at CpG+20, more preferably a methylated C fraction of 0.01 at CpG+20 or less is attributed to the non-response of said patient to a monoaminergic antidepressant. Accordingly, in a further embodiment of the invention a methylated C fraction of more than 0.01 at CpG+20 is attributed to the response of said patient to a monoaminergic antidepressant, preferably a methylated C fraction of more than 0.015 at CpG+20, more preferably a methylated C fraction of 0.02 or more at CpG+20 is attributed to the response of said patient to a monoaminergic antidepressant.

CpG+36

In one embodiment of the present invention a methylated C fraction of less than 0.02 at CpG+36 is attributed to the non-response of said patient to a monoaminergic antidepressant, preferably a methylated C fraction of less than 0.015 at CpG+36, more preferably a methylated C fraction of 0.01 at CpG+36 or less is attributed to the non-response of said patient to a monoaminergic antidepressant. Accordingly, in a further embodiment of the invention a methylated C fraction of more than 0.01 at CpG+36 is attributed to the response of said patient to a monoaminergic antidepressant, preferably a methylated C fraction of more than 0.015 at CpG+36, more preferably a methylated C fraction of 0.02 or more at CpG+36 is attributed to the response of said patient to a monoaminergic antidepressant.

CpG+42

In one embodiment of the present invention a methylated C fraction of less than 0.26 at CpG+42 is attributed to the non-response of said patient to a monoaminergic antidepressant, preferably a methylated C fraction of less than 0.25 at CpG+42, more preferably a methylated C fraction of 0.2 at CpG+42 or less is attributed to the non-response of said patient to a monoaminergic antidepressant. Accordingly, in a further embodiment of the invention a methylated C fraction of more than 0.2 at CpG+42 is attributed to the response of said patient to a monoaminergic antidepressant, preferably a methylated C fraction of more than 0.25 at CpG+42, more preferably a methylated C fraction of 0.26 or more at CpG+42 is attributed to the response of said patient to a monoaminergic antidepressant.

As described herein and documented in the appended examples, it has been surprisingly found that patients that respond to a treatment with a monoaminergic antidepressant have a significantly higher percentage of DNA molecules which are methylated at specific CpG sites of the BNDF-gene promoter, as compared to patients that do not respond to treatment with a monoaminergic antidepressant. For example, it has been shown that the methylated C fraction at the CpG island CpG−87 of the BDNF-gene exon-IV promoter is significantly higher in patients that respond to treatment with monoaminergic antidepressants than in patients that do not respond to treatment with monoaminergic antidepressants. Furthermore, in context of the present invention it has been found that monoaminergic antidepressants reduce the expression level of BDNF when the promoter of the BDNF-gene is not methylated.

Accordingly, in one embodiment of the inventive method for predicting the non-response or response to a monoaminergic antidepressant of a patient is performed before, during or after onset of treatment of the patient with the monoaminergic antidepressant. In a prioritized embodiment, the inventive methods for predicting the non-response or response to a monoaminergic antidepressant of a patient and/or the inventive stratification methods are performed before or during treatment of the patient with the monoaminergic antidepressant.

"Methylated C fraction" refers to the relative amount of methylated cytosines at a specific position, e.g. a specific CpG dinucleotide, of DNA molecules comprising the position (region) of the one or more CpG dinucleotides in the sample to be analysed. The calculation of the "methylated C fraction" is well known in the art and described, e.g. in Lewin et al. Quantitative DNA methylation analysis based on four-dye trace data from direct sequencing of PCR amplificates, Bioinformatics 2004; 20(17):3005-3012.

The methylated C fraction is a fraction of 1, i.e. a methylated C fraction of 0.03 refers 3% of DNA molecules comprised in the sample having 5-methyl-cytosine at the respective position or CpG dinucleotide.

Thus, the term "methylated C fraction" relates to the percentage of DNA molecules (in a sample) which is methylated at a specific cytosine. This specific cytosine may be a part of a specific CpG dinucleotide. For example, a methylated C fraction of 0.05 means that 5% of the DNA molecules (in a sample) are methylated at a specific cytosine, a methylated C fraction of 0.04 means that 4% of the DNA molecules (in a sample) are methylated at a specific cytosine and a methylated C fraction of 0.03 means that 3% of the DNA molecules (in a sample) are methylated at a specific cytosine.

For example, a methylated C fraction of 0.05 at CpG-87 means that 5% of the DNA molecules (in a sample) are methylated at CpG-87, a methylated C fraction of 0.04 at CpG-87 means that 4% of the DNA molecules (in a sample) are methylated at CpG-87 and a methylated C fraction of 0.03 at CpG-87 means that 3% of the DNA molecules (in a sample) are methylated at CpG-87.

Monoaminergic antidepressants are known by those of ordinary skills in the art. As been shown, the present invention provides a method for predicting the response to various representatives of the subgroups of monoaminergic antidepressants. Hence, in a preferred embodiment monoaminergic antidepressants are selected from the group consisting of selective serotonin reuptake inhibitors, selective serotonin-norepinephrine reuptake inhibitors, noradrenergic and specific serotonergic antidepressants, norepinephrine (noradrenaline) reuptake inhibitors, norepinephrine-dopamine reuptake inhibitors, selective serotonin reuptake enhancers, serotonin-norepinephrine-dopamine reuptake inhibitors, norepinephrine-dopamine disinhibitors, tricyclic antidepressants, monoamine oxidase inhibitors, and nicotine.

Preferably the monoaminergic antidepressant is selected from the group consisting of selective serotonin reuptake inhibitors (SSRI), selective serotonin and noradrenalin reuptake inhibitors (SNRI) selective noradrenaline and dopamine reuptake inhibitors, selective norepinephrine-dopamine reuptake inhibitors, monoamine oxidase inhibitors, tricyclic antidepressants, and other monoaminergic antidepressants, preferably the monoaminergic antidepressant is selected from the group consisting of venlafaxin, sertralin, mirtazapin, escitalopram, citalopram, fluoxetine, paroxetin, duloxetin, bupropion, amitriptylin, clomipramin, trimipramin, agomelatine and tranylcypromin. The skilled artisan will readily understand that the present invention provides the method, kit and uses allowing the prediction of the response to any of the above mentioned subgroups or active compounds.

As different diseases may be treated with different monoaminergic antidepressants the skilled artisan may decide on combinations of diseases the patient is suffering from and monoaminergic antidepressants. Such combinations are for example disclosed in the standard reference book for psychopharmaceuticals (Benkert, Hippius. Kompendium der Psychiatrischen Pharmakotherapie, 8. Auflage 2010, Springer Medizin Verlag Heidelberg). However, in one embodiment of the method according to the present invention the patient is suspected to have or is suffering from a panic disorder and the monoaminergic antidepressant is selected from the group consisting of citalopram, escitalopram, and paroxetin. In a further embodiment of the present invention the patient is suspected to have or is suffering from a social anxiety disorder or social phobia and the monoaminergic antidepressant is selected from the group consisting of escitalopram, and paroxetin. In a further embodiment the patient is suspected to have or is suffering from a bulimia nervosa and the monoaminergic antidepressant is fluoxetine. In yet a further embodiment of the present invention the patient is suspected to have an obsessive-compulsive disorder or is suffering from an obsessive-compulsive disorder and the monoaminergic antidepressant is selected from the group consisting of fluoxetin, fluvoxamin, paroxetin, and sertralin. In a further embodiment of the present invention the patient is suspected to have or is suffering from a post-traumatic stress disorder and the monoaminergic drug is selected from the group consisting of paroxetin, and sertralin. In a further embodiment the patient is suspected to have or is suffering from a generalized anxiety disorder and the monoaminergic antidepressant is paroxetine.

The patient who is suspected to have a depression or is suffering from a depression and who shows normal or hypermethylation of the BDNF-gene promoter may be treated with a monoaminergic antidepressant selected from the group consisting of selective serotonin reuptake inhibitors, selective serotonin-norepinephrine reuptake inhibitors, noradrenergic and specific serotonergic antidepressants, norepinephrine (noradrenaline) reuptake inhibitors, norepinephrine-dopamine reuptake inhibitors, selective serotonin reuptake enhancers, serotonin-norepinephrine-dopamine reuptake inhibitors, norepinephrine-dopamine disinhibitors, tricyclic antidepressants, monoamine oxidase inhibitors, and nicotine. Preferably said patient who is suspected to have a depression or who is suffering from a depression and who has normal or hypermethylation of the BDNF-gene promoter is treated with a monoaminergic antidepressant that is a selective serotonin reuptake inhibitor. In one embodiment the patient who is suspected to have a depression or who is suffering from a depression and who has normal or hypermethylation of the BDNF-gene promoter is treated with a monoaminergic antidepressant that is selected from the group consisting of venlafaxin, sertralin, mirtazapin, escitalopram, citalopram, fluoxetine, paroxetin, duloxetin, bupropion, amitriptylin, clomipramin, trimipramin, agomelatine and tranylcypromin.

In a certain preferred embodiment of the present invention a methylated C fraction of less than 0.05 at CpG-87 is attributed to the non-response of said patient to a monoaminergic antidepressant, preferably a methylated C fraction of less than 0.04 at CpG-87, more preferably a methylated C fraction of 0.03 at CpG-87 or less is attributed to the non-response of said patient to a monoaminergic antidepressant selected from the group consisting of venlafaxin, sertralin, mirtazapin, escitalopram, citalopram, fluoxetine, paroxetin, duloxetin, bupropion, amitriptylin, clomipramin, trimipramin, agomelatine and tranylcypromin. Accordingly, in a further embodiment of the invention a methylated C fraction of more than 0.03 at CpG-87 is attributed to the response of said patient to a monoaminergic antidepressant, preferably a methylated C fraction of more than 0.04 at CpG-87, more preferably a methylated C fraction of 0.05 or more at CpG-87 is attributed to the response of said patient to a monoaminergic antidepressant selected from the group consisting of venlafaxin, sertralin, mirtazapin, escitalopram, citalopram, fluoxetine, paroxetin, duloxetin, bupropion, amitriptylin, clomipramin, trimipramin, agomelatine and tranylcypromin. In a certain preferred embodiment of the present invention a methylated C fraction of less than 0.05 at CpG-87 is attributed to the non-response of said patient to a monoaminergic antidepressant selected from the group consisting of venlafaxin, sertralin, mirtazapin, escitalopram, citalopram, fluoxetine, paroxetin, duloxetin, bupropion, amitriptylin, clomipramin, trimipramin and tranylcypromin, and a methylated C fraction of 0.05 or more at CpG−87 is attributed to the response of said patient to a monoaminergic antidepressant selected from the group consisting of venlafaxin, sertralin, mirtazapin, escitalopram, citalopram, fluoxetine, paroxetin, duloxetin, bupropion, amitriptylin, clomipramin, trimipramin, agomelatine and tranylcypromin.

Various assays to determine the methylation status of DNA are known in the art, and can be used in conjunction with the present invention. These assays rely on two distinct approaches: bisulfite conversion based approaches and non-bisulfite based approaches. Non-bisulfite based methods for analysis of DNA methylation reply on the inability of methylation-sensitive enzymes to cleave methylation cytosines in their restriction.

The bisulfite based methods use the bisulfite conversion of unmethylated cytosines in DNA. The bisulfite conversion relies on treatment of DNA samples with sodium bisulfite which converts unmethylated cytosine to uracil, while methylated cytosines are maintained (Furuichi et al., Biochem Biophys Res Commun. 1970; 41: 1185-91). This conversion results in a change in the sequence of the original DNA. DNA methylation analysis has been performed successfully with a number of techniques including: sequencing, methylation-specific PCR (MSP), melting curve methylation-specific PCR (McMSP), MLPA with or without bisulfite treatment, QAMA (Zeschnigk et al. Nucleic Acids Res. 2004; 32: e125), MSRE-PCR (Melnikov et al. Nucleic Acids Res. 2005; 33: e93), MethyLight (Eads et al. Nucleic Acids Res. 2000; 28: E32), ConLight-MSP (Rand et al. Methods. 2002; 27: 114-20), bisulfite conversion-specific methylation-specific PCR (BS-MSP) (Rand et al. Methods. 2002; 27: 114-20), COBRA (which relies upon use of restriction enzymes to reveal methylation dependent sequence differences in PCR products of sodium bisulfite-treated DNA), methylation-sensitive single-nucleotide primer extension conformation (MS-SNuPE), methylation-sensitive single-strand conformation analysis (MS-SSCA), Melting curve combined bisulfite restriction analysis (McCOBRA) (Akey et al. Genomics. 2002; 80: 376-84), PyroMethA, HeavyMethyl (Cottrell et al. Nucleic Acids Res. 2004; 32: e10), MALDI-TOF, MassARRAY, Quantitative analysis of methylated alleles (QAMA), enzymatic regional methylation assay (ERMA), QBSUPT, MethylQuant, Quantitative PCR sequencing and oligonucleotide-based microarray systems, Pyrosequencing, Meth-DOP-PCR and Bisulfite based next generation sequencing. A review of some useful techniques is provided in Nucleic acids research, 1998, Vol. 26, No. 10, 2255-2264, Nature Reviews, 2003, Vol. 3, 253-266; Oral Oncology, 2006, Vol. 42, 5-13, which references are incorporated herein in their entirety. Any of these techniques may be utilised in accordance with the present invention, as appropriate.

Additional methods for the identification of methylated CpG dinucleotides utilize the ability of the methyl binding domain (MBD) of the MeCP2 protein to selectively bind to methylated DNA sequences (Cross et al. Nat. Genet. 1994; 6: 236-44; Shiraishi et al. Biol. Chem. 1999; 380: 1127-31). Alternatively, the MBD may be obtained from MBP, MBP2, MBP4 or poly-MBD (Jorgensen et al. Nucleic Acids Res. 2006; 34: e96). In one method, restriction exonuclease digested genomic DNA is loaded onto expressed His-tagged methyl-CpG binding domain that is immobilized to a solid matrix and used for preparative column chromatography to isolate highly methylated DNA sequences. Such methylated DNA enrichment-step may supplement the methods of the invention. Several other methods for detecting methylated CpG dinucleotides and/or islands are well known in the art and include amongst others methylated-CpG island recovery assay (MIRA).

A further method for determining the methylation status is methylation sensitive enzymatic digestion (Bleich S, Lenz B, Ziegenbein M, Beutler S, Frieling H, Kornhuber J, et al. (2006). Epigenetic DNA hypermethylation of the HERP gene promoter induces down-regulation of its mRNA expression in patients with alcohol dependence (Alcohol Clin. Exp. Res., 30(4), 587-591). In one of these assays restriction length polymorphisms of a DNA region of interest is performed using methylation sensitive restriction enzymes. Such enzymes cleave the DNA at the recognition sequence dependent on the methylation status of the DNA at said sequence. Hence, for example methylated DNA is not cleaved while non methylated DNA is resulting in different lengths and consequently different mobility in polymeric gels of the fragments. These fragments may be detected by several techniques known by those of ordinary skills in the art, e.g. ethidium bromide stain, southern blot, etc. Any of these methods may be employed in the present invention where desired. In specific embodiments, the methylation status of a brain-derived neurotrophic factor (BDNF)-gene promoter (or fragments thereof, especially the CpG islands, as discussed herein) is determined using methylation specific PCR (MSP), or an equivalent amplification technique. The MSP technique will be familiar to one of skill in the art. In the MSP approach, DNA may be amplified using primer pairs designed to distinguish methylated from unmethylated DNA by taking advantage of sequence differences as a result of sodium-bisulfite treatment (Herman et al. Proc Natl Acad Sci USA. 1996; 93: 9821-6 and WO 97/46705).

A specific example of the MSP technique is designated realtime quantitative MSP (qMSP), which permits reliable quantification of methylated DNA in real time. These methods are generally based on the continuous optical monitoring of an amplification procedure and utilise fluorescently labelled reagents whose incorporation in a product can be quantified and whose quantification is indicative of copy number of that sequence in the template. One such reagent is a fluorescent dye, called SYBR Green I that preferentially binds double-stranded DNA and whose fluorescence is greatly enhanced by binding of double-stranded DNA. Alternatively, labelled primers and/or labelled probes can be used. They represent a specific application of the well known and commercially available real-time amplification techniques such as hydrolytic probes (TAQMAN®), hairpin probes (MOLECULAR BEACONS®), hairpin primers (AMPLIFLUOR®), hairpin probes integrated into primers (SCORPION®), oligonucleotide blockers (such as the HeavyMethyl™ technique) and primers incorporating complementary sequences of DNAzymes (DzyNA®), specific interaction between two modified nucleotides (Plexor™) etc., as described in more detail herein. Often, these real-time methods are used with the polymerase chain reaction (PCR). In HeavyMethyl™, described for example in WO02/072880 the priming is methylation specific, but non-extendable oligonucleotide blockers provide this specificity instead of the primers themselves. The blockers bind to bisulfite-treated DNA in a methylation-specific manner, and their binding sites overlap the primer binding sites. When the blocker is bound, the primer cannot bind and therefore the amplicon is not generated. Heavymethyl can be used in combination with real-time or end point detection in the methods of the invention.

All of the recited methods may be used for determining the methylation status of said BDNF-gene promoter. In a preferred embodiment of the present invention the methylation status is determined using bisulfite sequencing, pyrosequencing, MALDI-TOF, methylation sensitive enzymatic digestion, and qMSP.

In a certain preferred embodiment the methylation status of said BDNF-gene promoter is determined using bisulfite sequencing. In a yet further preferred embodiment the determination of BDNF-gene exon-IV promoter is determined using bisulfite sequencing, preferably using the sequencing primer having at least 70% identity to SEQ ID NO. 5, preferably at least 80% identity, more preferably at least 90% identity, even more preferably at least 95% identity, yet more preferably at least 99% identity. In a further preferred embodiment the sequencing primer has the sequence of SEQ ID NO. 5. It will be readily appreciated by those skilled in the art that the DNA may be amplified after treatment with bisulfite and before sequencing.

Hence, in a preferred embodiment at least a part of the BDNF-gene exon-IV promoter is amplified after treatment with bisulfite and before sequencing, preferably using at least two primers comprising the sequence of SEQ ID NO. 2 and SEQ ID NO. 4, respectively, or comprising a sequence having at least 70% identity thereto, preferably at least 80% identity, more preferably at least 90% identity, even more preferably at least 95% identity, yet more preferably at least 99% identity. In a further embodiment amplification is accomplished using semi-nested PCR with three primers having at least 70% identity to SEQ ID NO. 2, SEQ ID NO. 3 and SEQ ID NO. 4, preferably at least 80% identity, more preferably at least 90% identity, even more preferably at least 95% identity, yet more preferably at least 99% identity.

Oligonucleotides, such as primers, or polynucleotides may be prepared using any suitable method, such as, for example, the phosphotriester and phosphodiester methods or automated embodiments thereof. In one such automated embodiment diethylophosphoramidites are used as starting materials and may be synthesized as described by Beaucage et al., Tetrahedron Letters, 22:1859-1862 (1981), which is hereby incorporated by reference. One method for synthesizing oligonucleotides on a modified solid support is described in U.S. Pat. No. 4,458,006, which is hereby incorporated by reference. It is also possible to use a primer which has been isolated from a biological source (such as a restriction endonuclease digest).

Preferred primers have a length of from about 15-100, more preferably about 20-50, most preferably about 20-40 bases.

In a specific, non-limiting embodiment the present invention relates to a method for predicting the non-response or response to a monoaminergic antidepressant of a patient suffering from depression comprising the steps: (i) determining the DNA-methylation status of at least CpG-87 at BDNF-gene exon-IV promoter (SEQ ID NO. 1) in a sample of said patient; (ii) attributing a hypomethylation of said BDNF-gene promoter to the non-response to a monoaminergic antidepressant of said patient; and (iii) attributing normal methylation or hypermethylation of said BDNF-gene promoter to the response to a monoaminergic antidepressant of said patient; whereby the methylation status in step (i) is determined by bisulfite sequencing, preferably using semi nested PCR with amplification primers having the sequence of SEQ ID NO. 2, SEQ ID NO. 3, and SEQ ID NO. 4; and a sequencing primer having the sequence of and SEQ ID NO. 5, wherein a methylated C fraction of less than 0.05 at CpG-87 is attributed to the non-response of said patient to a monoaminergic antidepressant selected from the group consisting of venlafaxin, sertralin, mirtazapin, escitalopram, citalopram, fluoxetine, paroxetin, duloxetin, bupropion, amitriptylin, clomipramin, trimipramin and tranylcypromin, and a methylated C fraction of 0.05 or more at CpG-87 is attributed tot the response of said patient to a monoaminergic antidepressant selected from the group consisting of venlafaxin, sertralin, mirtazapin, escitalopram, citalopram, fluoxetine, paroxetin, duloxetin, bupropion, amitriptylin, clomipramin, trimipramin and tranylcypromin.

As outlined above, the method according to the present invention allows the prediction of the response or non-response to a monoaminergic antidepressant prior to the onset of treatment with said antidepressant. Hence, in one embodiment of the method according to the present invention the steps including steps (i), (ii) and (iii) as outlined above are performed before administration of a monoaminergic antidepressant.

In one embodiment of the method according to the present invention the steps including steps (i), (ii) and (iii) as outlined above are performed during or after administration of a monoaminergic antidepressant. It is prioritized that the method of the present invention is performed before or during therapy with a monoaminergic antidepressant.

The skilled person is aware of alternative therapies and treatments of depression. Hence, he is able to decide how to treat a patient if the method according to the present invention predicts the non-response of said patient to a monoaminergic antidepressant. He may for example follow the S3 guidelines of the German society for psychiatry, psychotherapy and neurology (Deutsche Gesellschaft für Psychiatrie, Psychotherapie and Nervenheilkunde (DGPPN)). In such case augmentation with lithium or $2^{nd}$ generation antipsychotics would be appropriate. Alternatively a combination of different antidepressants may be administered to the patient or the patient may be treated with electro convulsive therapy (ECT). According to the mentioned guidelines of the DGPPN, patients having an episode of severe depression may be treated with psychotherapy in addition or as an alternative. Further therapies may also be applied like light therapy, sleep deprivation and/or sportive activities.

In one embodiment of the method according to the present invention the sample is obtained from the patient before step (i), i.e. before the methylation/DNA-methylation status of the BDNF-gene promoter is determined).

A "sample" in the meaning of the invention can be all biological tissues and all fluids from the patient such as lymph, urine and/or cerebral fluid. Tissues may be, e.g. epithelium tissue, connective tissue such as bone or blood, muscle tissue such as visceral or smooth muscle and skeletal muscle and nervous tissue. The sample is collected from the patient and subjected to the method according to the invention. Where appropriate, as for instance in the case of solid samples, the sample may need to be solubilized, homogenized, or extracted with a solvent prior to use in the present invention in order to obtain a liquid sample. A liquid sample hereby may be a solution or suspension, as for example lymph, blood or serum. Liquid samples may be subjected to one or more pre-treatments prior to use in the present invention. Such pre-treatments include, but are not limited to dilution, filtration, centrifugation, concentration, sedimentation, precipitation and/or dialysis. Pre-treatments may also include the addition of chemical or biochemical substances to the solution, such as acids, bases, buffers, salts, solvents, reactive dyes, detergents, emulsifiers, and/or chelators. "Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood) for at least 15 minutes at 2000 to 3000 g. "Serum" in the context of the present invention is the undiluted, extracellular portion of blood after adequate coagulation is completed. Coagulation is usually completed after 30 min. Serum can be obtained by centrifugation of the coagulated sample for at least 10 minutes at a minimum speed of 1500 g. "blood" is a venous, arterial or capillary blood sample in which the concentrations and properties of cellular and extra-cellular constituents remain relatively unaltered when compared with their in-vivo state. Anticoagulation in-vitro stabilizes the constituents in a whole blood sample for a certain period of time.

Preferably the sample is a liquid sample, more preferably a sample selected from the group consisting of blood, serum, plasma, saliva, sputum and cerebrospinal fluid, more preferred are blood, serum, or plasma.

The present invention also relates to a kit for determining whether a patient suffering from depression is a non-responder to monoaminergic antidepressant comprising:
  means for determining the methylation status of DNA; and
  at least one primer pair for amplifying a BDNF-gene promoter or a fragment thereof.

As used herein, a kit is a packaged combination optionally including instructions for use of the combination and/or other reactions and components for such use. Particularly the kit in one embodiment comprises instructions for performing the method according to the present invention as outlined herein above. The embodiment outlined above for the method according to the present invention apply also to the kit as well as to the instruction manual optionally comprised in the kit according to the present invention. In one embodiment the kit comprises a manual, wherein the manual comprises control data for determining whether the DNA of a BDNF-gene promoter is hypomethylated, normal methylated or hypermethylated. As outlined above the inventors found preferred thresholds for a methylated C fraction. The embodiments outlined above for the methylated C fractions for different CpG dinucleotides apply for the manual of the kit as well. In a certain preferred embodiment the kit comprises a manual, wherein the manual comprises data or advises indicating that a methylated C fraction of less than 0.05 at CpG–87 is attributed to the non-response of said patient to a monoaminergic antidepressant selected from the group consisting of venlafaxin, sertralin, mirtazapin, escitalopram, citalopram, fluoxetine, paroxetin, duloxetin, bupropion, amitriptylin, clomipramin, trimipramin and tranylcypromin, and a methylated C fraction of 0.05 or more at CpG–87 is attributed to the response of said patient to a monoaminergic antidepressant selected from the group consisting of venlafaxin, sertralin, mirtazapin, escitalopram, citalopram, fluoxetine, paroxetin, duloxetin, bupropion, amitriptylin, clomipramin, trimipramin and tranylcypromin.

The embodiments disclosed in connection with the method for predicting the non-response or response to a monoaminergic antidepressant of a patient to be treated with a monoaminergic antidepressant apply, mutatis mutandis, to the kit of the present invention.

Advantageously, the kit of the present invention further comprises, optionally (a) reaction buffer(s), storage solutions, wash solutions and/or remaining reagents or materials required for the conduction of the assays as described herein. Furthermore, parts of the kit of the invention can be packaged individually in vials or bottles or in combination in containers or multicontainer units. These vials/bottles/containers or multicontainers may, in addition to the primer pair as described herein, comprise preservatives or buffers for storage.

The kit of the present invention may be advantageously used, inter alia, for carrying out the stratification method as described herein and/or it could be employed in a variety of further applications, e.g., as diagnostic kit, as research tool or as therapeutic tool. Additionally, the kit of the invention may contain further means for detection suitable for scientific, medical and/or diagnostic purposes. The manufacture of the kit of the present invention follows preferably standard procedures which are known to the person skilled in the art.

As outlined above for the method according to the present invention, the methylation status of CpG–87 is itself predictive for the response or non-response in the method according to the present invention. Hence, in a preferred embodiment of the kit according to the present invention the at least one primer pair is suitable for amplifying the BDNF-gene exon-IV promoter, preferably for amplifying a fragment of said promoter, wherein said fragment comprises at least CpG island CpG–87. Such primer can be constructed by those skilled in the art. However, a preferred primer pair for amplifying said fragment comprises the sequence of SEQ ID NO. 2 and SEQ ID NO. 4, respectively, or comprises a sequence having at least 70% identity thereto, preferably at least 80% identity, more preferably at least 90% identity, even more preferably at least 95% identity, yet more preferably at least 99% identity.

In a preferred embodiment the primers of the primer pair have at least 70% identity to SEQ ID NO. 2 and SEQ ID NO. 4, preferably at least 80% identity, more preferably at least 90% identity, even more preferably at least 95% identity, yet more preferably at least 99% identity. Further preferred is a primer pair having the sequences of SEQ ID NO. 2 and SEQ ID NO. 4. In a further preferred embodiment the amplification is performed in a semi-nested PCR using primers of SEQ ID NO. 2, SEQ ID NO. 3 and SEQ ID NO. 4.

Methods and accordingly means for determining the methylation status of DNA are known by those skilled in the art as outlined in great detail herein above. These may for example include methylation sensitive restriction enzymes, probes, dNTPs, buffers etc. It will be apparent for those of ordinary skills that the means for determining the methylation status of DNA may be chosen depending on the method acquired. As outlined above in a preferred embodiment bisulfite based methods for determining the methylation status are used. Hence, in a preferred embodiment of the kit according to the present invention the means for determining the methylation status of DNA comprise bisulfite, preferably sodium bisulfite. Furthermore, the kit may comprise a sequencing primer, preferably a primer having a sequence at least 70% identical to SEQ ID NO. 5, preferably at least 80% identity, more preferably at least 90% identity, even more preferably at least 95% identity, yet more preferably at least 99% identity. In a further embodiment the sequencing primer has the sequence of SEQ ID NO. 5.

Furthermore, the present invention relates to the use of a kit according to the present invention in a method according to the present invention.

It will be apparent that the methods and components of the present invention, as well as the uses as substantially described herein or illustrated in the description and the examples, are also subject of the present invention and claimed herewith. In this respect, it is also understood that the embodiments as described in the description and/or any one of the examples, can be independently used and combined with any one of the embodiments described hereinbefore and claimed in the appended claims set. Thus, these and other embodiments are disclosed and encompassed by the description and examples of the present invention.

The present invention is illustrated by the following Figures and Examples.

FIGURE LEGENDS

FIG. 1: Fraction of methylated cytosines at CpG−87 in the BDNF-gene exon-IV promoter. (A) In samples from non-responders and responders. Bars indicate the standard deviation; (Mann-Whitney-U: 360; P=0.002; Padj.=0.02); (B) In samples from patients with non-remission and remission. Bars indicate the standard deviation; (Mann-Whitney-U: 297 P=0.003; Padj.=0.03).

Figure 2:
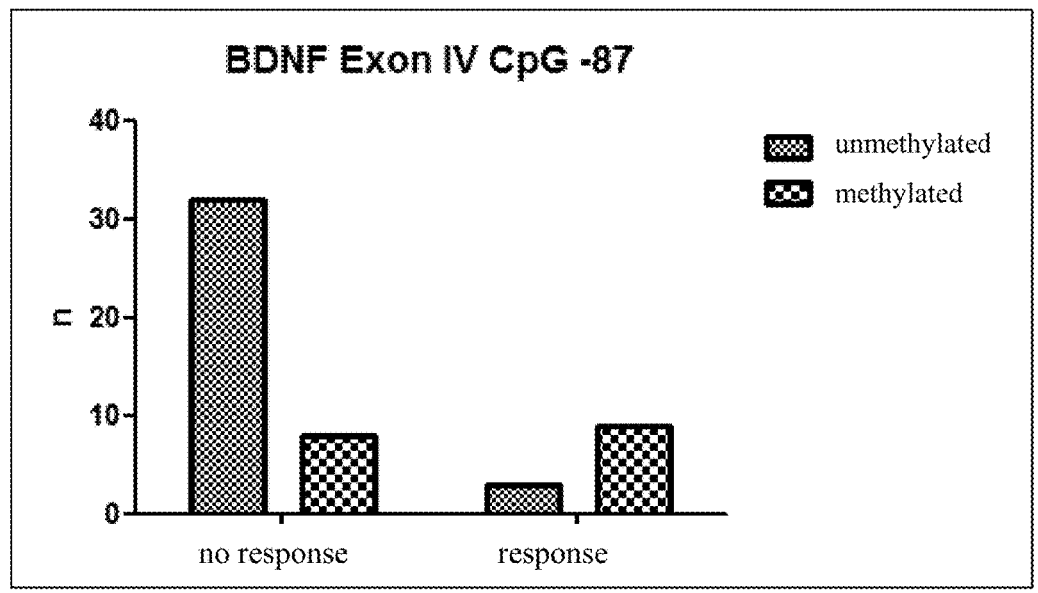
Figure 2:
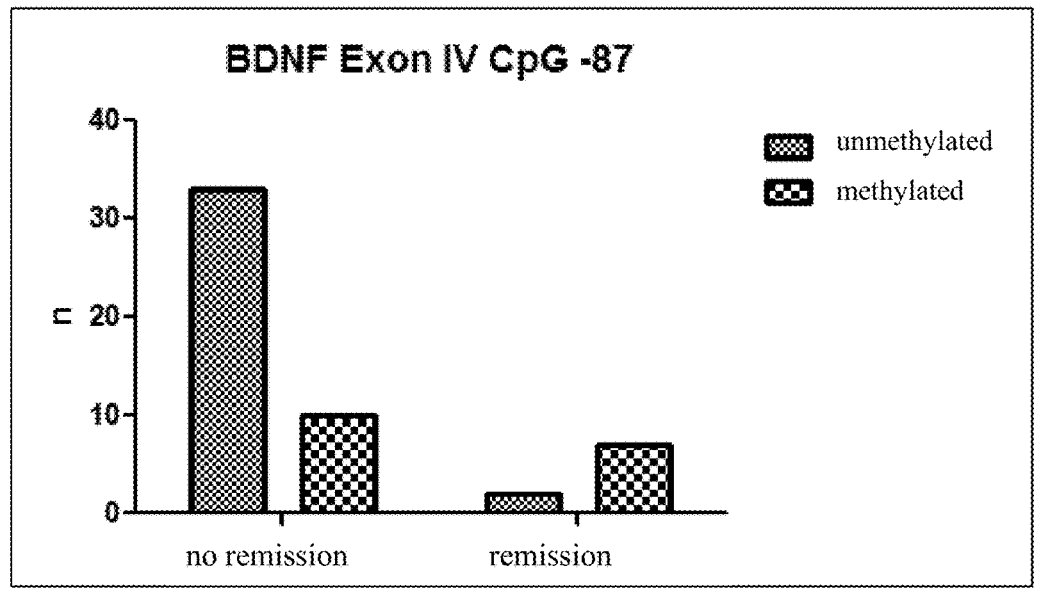
Figure 2:
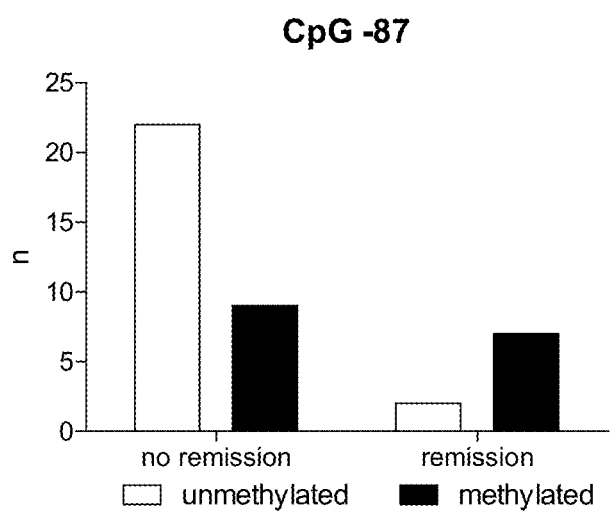

FIG. 2: Fraction of patients with hypomethylated, or normal and hypermethylated DNA at CpG−87. (A) Patients with response or non-response. The Odd ratio for a non-response after six weeks of treatment if CpG−87 was hypomethylated before the treatment is 12. (95% confidence interval: 2.63-54.82; p=0.002); (B) patients with remission or non-remission. The Odd ratio for a non-response after six weeks of treatment if CpG−87 was hypomethylated before the treatment is 11,55. (95% confidence interval: 2.07-64.72; p=0.005).

Figure 3:
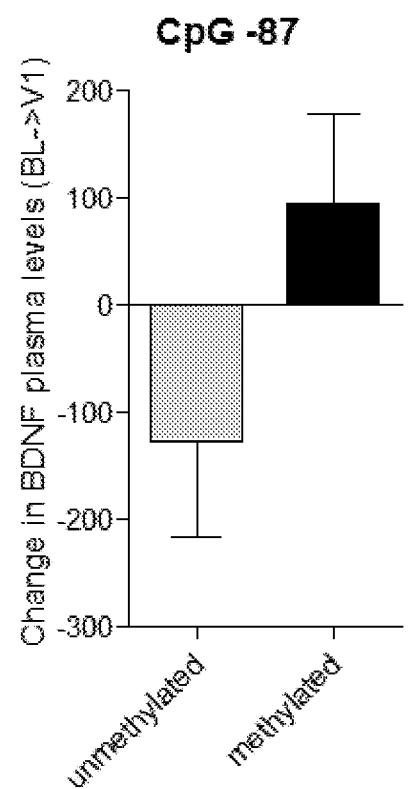

FIG. 3: Normal or hypermethylation of CpG−87 is associated with early increase of plasma BDNF levels. Shown is the change in BDNF plasma level after 1 week compared to plasma levels before onset of the treatment (in pg/ml (T-test: T=2.28, p=0.028).

Figure 4:
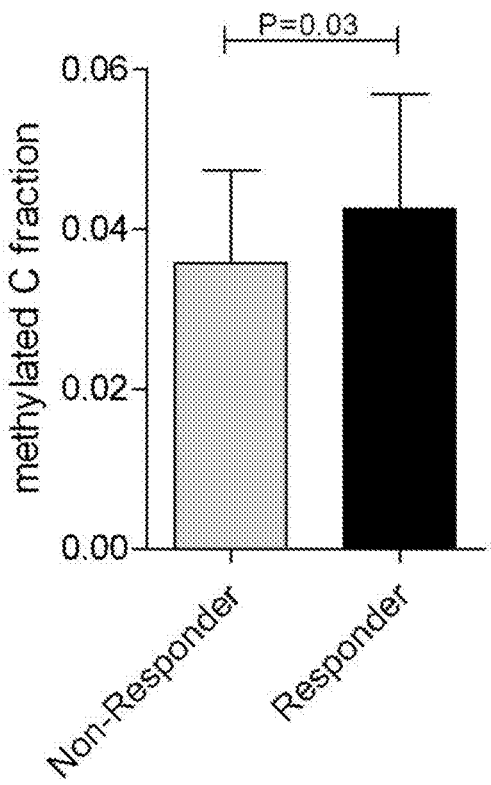
Figure 4:
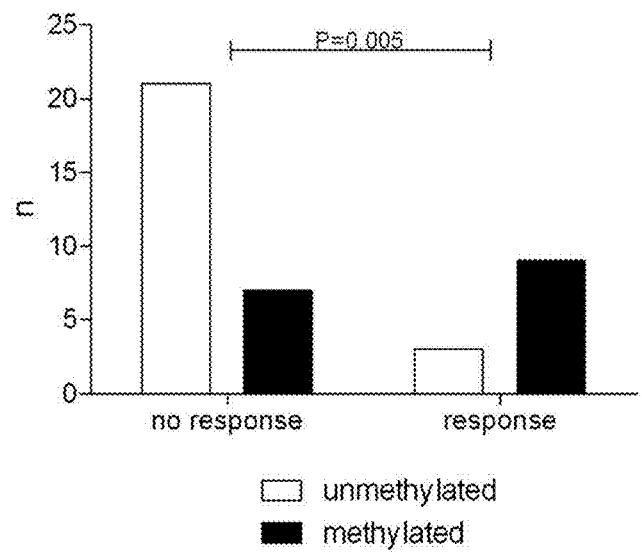
Figure 4:
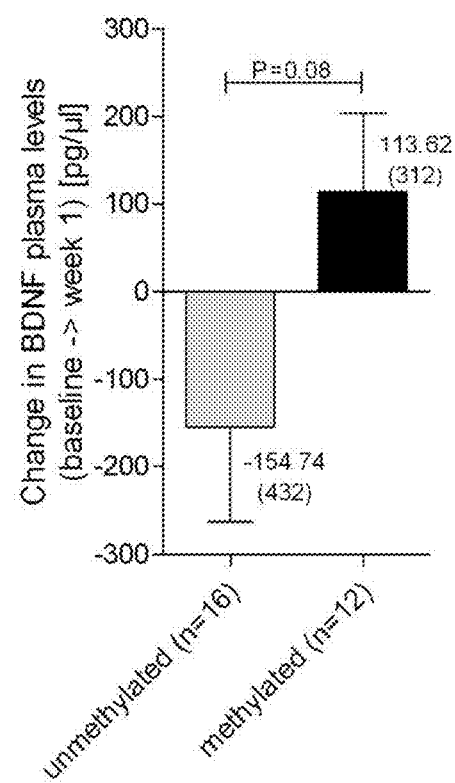
Figure 4:
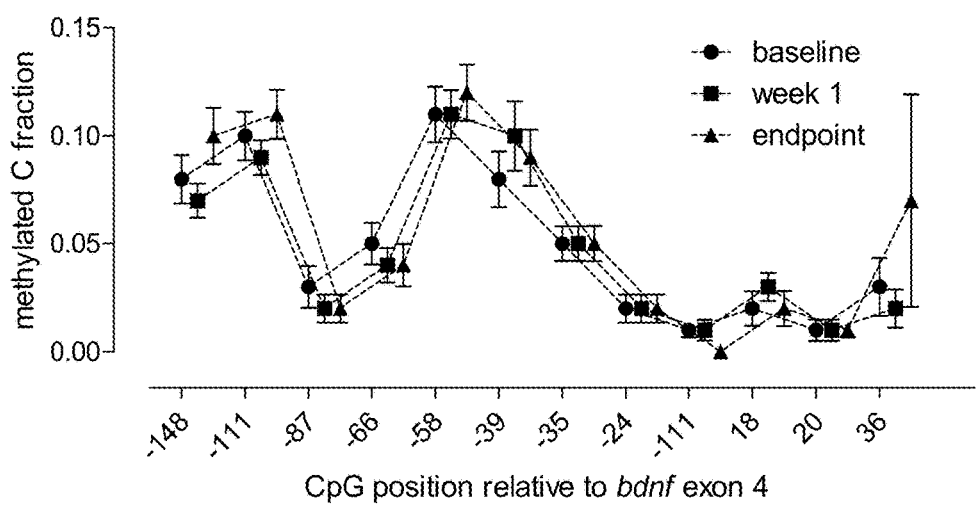
Figure 4:
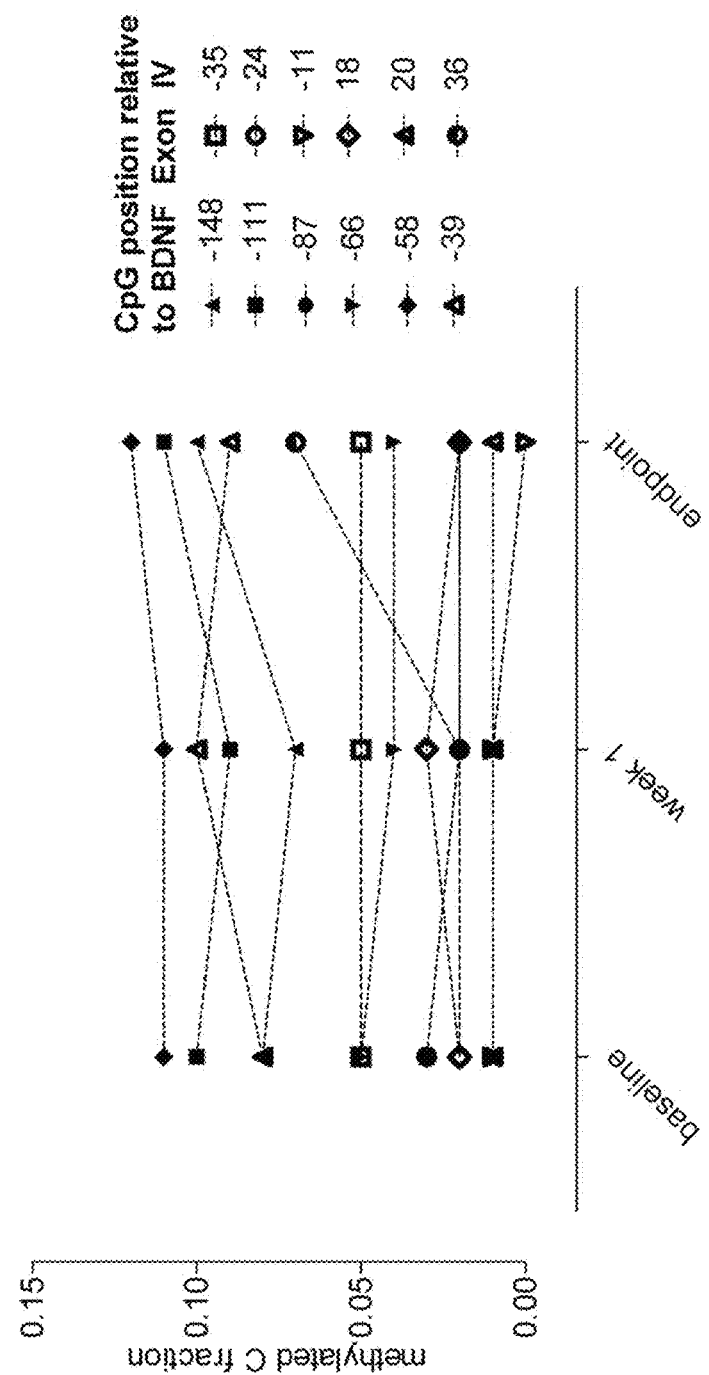
Figure 4:
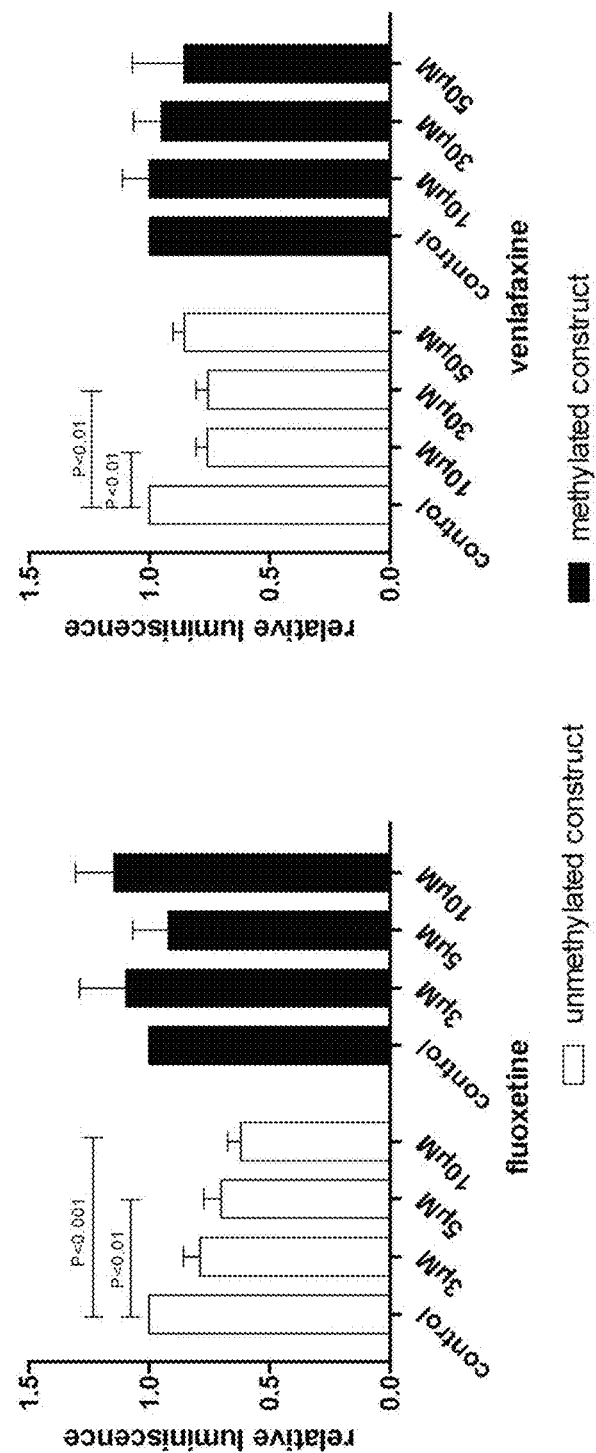

FIG. 4: DNA methylation at BDNF-gene exon-IV promoter CpG position −87 significantly differs between final responders and non-responders. (A) DNA methylation at BDNF-gene exon-IV promoter CpG position −87 (relative to first nucleotide of exon-IV) significantly differs between final responders and non-responders (Mann-Whitney-U: 151; P=0.03). (B) Dichotomized methylation levels (no methylation vs. any methylation) show a high predictive value for final non-response. (Fisher's test: OR (no response if not methylated)=9.00, 95%-CI=1.887 to 42.92; P=0.005) Significance data is shown for the difference between the bars "methylated/no response" and "unmethylated/response" (C) Plasma BDNF levels drop in the unmethylated group during first week of treatment, while it increases in the group showing any methylation at BDNF-gene exon-IV promoter—CpG position −87. (T-Test: T=1.82; df=26; P=0.08) Numbers given in the figure represent mean (±SD). BDNF plasma levels and DNA methylation measurements were only available in 28 patients. (D) DNA methylation of the BDNF-gene exon-IV promoter does not significantly change during antidepressant treatment. (E) in vitro changes of luminescence of a BDNF-gene exon-IV promoter construct subcloned in a pGL4.14 luciferase reporter plasmid and transfected into SH-SY5Y neuroblastoma cell line. Some constructs were artificially methylated using sss1-methylase and SAM. Incubation with fluoxetine or venlafaxine for 48 h leads to a decrease of reporter gene activity only in those experiments with an unmethylated construct (Repeated Measurements-ANOVA: Fluoxetine unmethylated: F=9.24; df=3; P=0.0019; Fluoxetine methylated: F=0.45; df=3; P=0.72; Venlafaxine unmethylated: F=7.15; df=3; P=0.0029; Venlafaxine methylated: F=0.25; df=3; P=0.86; P-values given in the figure are derived from Dunnett's Multiple Comparison Test).

TABLE 2

Sequences disclosed herein

| SEQ ID NO. | Sequence | Name and Comments |
|---|---|---|
| 1 | 5'-TTTGCTGGGGCTGGAAGTGAAAACATCTGCA AAAGCATGCAATGCCCTGGAACGGAACTCTTCTA ATAAAAGATGTATCATTTTAAATGCGCTGAATTT TGATTCTGGTAATTCGTGCACTAGAGTGTCTATT TCGAGGCAGCGGAGGTATCATATGACAGCGCACG TCAAGGCACCGTGGAGCCCTCTCGTGGACTCCCA CCCACTTTCCCATTCACCGCGGAGAGGGCTGCTC TCGCTGCCGCTCCCCCCGGCGAACTAGCATGAAA TCTCCCTGC-3' | Preferred sequence of the BDNF-gene exon-IV promotor |
| 2 | 5'-GGGGGAGGATTAATTGAGTTAGTTTTG-3' | BDNF_IV_forw1 (also designated as bisBDNF_IV_forw1, preferred forward primer for amplifying BDNF-gene exon-IV promoter) |
| 3 | 5'-TTTGTTGGGGTTGGAAGTGAAAAT-3' | BDNF_IV_forw2 (also designated as bisBDNF_IV_forw2, preferred nested forward primer for amplifying BDNF-gene exon-IV promoter) |
| 4 | 5'-ATATATACTCCTTCTATTCTACAACAA-3' | BDNF_IV_rev (also designated as bisBDNF_IV_rev, preferred reverse primer for amplifying BDNF-gene exon-IV promoter) |
| 5 | 5'-ACAAAAAAATTTCATACTAA-3' | BDNF_IV_seq (preferred sequencing primer for the BDNF-gene exon-IV promoter) |

TABLE 2-continued

Sequences disclosed herein

| SEQ ID NO. | Sequence | Name and Comments |
|---|---|---|
| 6 | 5'-CCCACCTTTTCAGTCACTACTTGTCAAAGTAACC-3' | BDNF4promR_362 (Oligonucleotide used as primer) |
| 7 | 5'-TTCCTCTGATACCCAGTGTTGTACCCCAAGA-3' | BDNF4promF_361 (Oligonucleotide used as primer) |
| 8 | 5'-TGGCCTCGGCGGCCATTCCTCTGATACCCAGTGT-3' | INpGL4.14_F_366 (Oligonucleotide used as primer) |
| 9 | 5'-CCGGATTGCCAAGCTCCCACCTTTTCAGTCACT-3' | INpGL4.14_R_378 (Oligonucleotide used as primer) |
| 10 | 5'-TGGCCGGTACCTGAGCTCGCTA-3' | pGL4.14seq_F_380 (Oligonucleotide used as primer) |
| 11 | 5'-GCATCTTCCATGGTGGCTTTA-3' | pGL4.14seq_R_381 (Oligonucleotide used as primer) |

EXAMPLES

Material and Methods

Participants and Study Design

Male and female inpatients of the Department of Psychiatry and Psychotherapy at the University Medical Centre Mainz for the treatment of Major Depressive Disorder (MDD) participated in present study. Hospitalisation of patients can occur after referral from the treating general practitioner, from the treating psychiatrist in the outpatients sector, from another hospital (e.g. after treatment in an intensive care unit in case of suicide attempt) or immediately after consultation of the departments' physician in charge. In general, the indication for emergent hospitalisation in a department of psychiatry is given in case of acute suicidality or risk of acute endangerment for others as well as in case of prominent psychotic symptoms. Typical indications for hospitalisation of patients with Major Depression are a severity of depression exceeding the capacity of outpatient care including suicidality, the risk of isolation due to depression and other severe psychosocial factors, life circumstances, which significantly impair the treatment success, resistance to outpatient treatment, high risk for (further) transition into chronicity of the disease. The patient sample consisted of the same patients as described in Tadić et al. Prog Neuropsychopharmacol Biol Psychiatry. 2011; 35: 415-20. All patients gave their written informed consent after a complete description of the study. The study was approved by the local ethics committee of the Landesärztekammer Rheinland-Pfalz and is compliant with the Code of Ethics of the World Medical Association (Declaration of Helsinki) The recruitment procedure of this study has been previously described in detail (Tadić et al. Prog Neuropsychopharmacol Biol Psychiatry. 2011; 35: 415-20). In brief, the study design was guided by the principle that results should be representative for inpatients with MDD; therefore, broad in/exclusion criteria were used. Inclusion criteria were i) Major Depressive Episode according to the Diagnostic and Statistical Manual of Mental Disorders (DSM-IV, American Psychiatric Association, 2000); ii) age between 18 and 65 years and 60 years at the beginning of the first depressive episode; iii) no treatment with an antidepressant medication or insufficient treatment response to an eventually existing antidepressant pre-medication (treatment duration>14 days), which was determined during a clinical interview at admission to the hospital by at least one specialist in psychiatry and at least one psychiatric resident; thus, all patients were about to be commenced or changed an antidepressant pharmacotherapy at the time of inclusion; iv) written informed consent to study participation. Exclusion criteria were i) lifetime diagnosis of dementia, schizophrenia, schizoaffective disorder, or bipolar disorder according to DSM-IV; ii) current diagnosis of alcohol dependency (DSM-IV) requiring acute detoxification; iii) depression due to organic factors including Parkinson's disease or Multiple Sclerosis; iv) pregnancy or breast-feeding; v) cognitive impairment (assessed clinically), which precludes a correct psychometric assessment. Diagnosis of MDD according to DSM-IV criteria were ascertained by at least one specialist and one resident in psychiatry. One of two research assistants, who had been trained in several rater trainings prior to the start of the study, additionally applied the German Version of the MINI International Neuropsychiatric Interview (Sheehan et al. J Clin Psychiatry. 1998; 59 Suppl 20: 22-33; quiz 34-57), During the study period the following antidepressants were given: Escitalopram (10 to 20 mg/d), sertraline (50 to 150 mg/d), fluoxetine (20 mg/d), venlafaxine (150 to 375 mg/d), duloxetine (90 to 120 mg/d), mirtazapine (30 to 45 mg/d), tranylcypromine (30 mg/d), amitriptyline (225 mg/d), clomipramine (150 mg/d), or trimipramine (100 mg/d). Severity of depression was weekly assessed by the 21-item Hamilton Depression Rating Scale (HAMD-21) from baseline to day 42, which was applied by one of two trained (Wagner et al., 2011) research assistants.

BDNF Plasma Level Measurement

Whole blood was obtained in a lithium-heparin tube from the antecubital vein from baseline to day 42 in weekly intervals between 08.00 and 11.00 am. After a maximum time of 30 min, whole blood was centrifuged at 1000 g at 4° C. to separate plasma. Plasma was then pipetted in small Eppendorf tubes; these were centrifuged at 10,000 g and at 4° C. Plasma was kept at −80° C. before assaying BDNF concentration with an enzyme-linked immunosorbent assay kit (R&D Systems, Wiesbaden, Germany). 100 ml assay diluent and 50 ml BDNF standard or 50 ml thawed sample were added. After incubation for 2 h at room temperature, 100 ml of mouse monoclonal antibody against BDNF conjugated to horseradish peroxidase were added and incubated for 1 h at room temperature. The plates were washed using an autowasher and the appropriate wash buffer. After the third wash, any remaining wash buffer was removed. 200 ml of substrate solution consisting of colour reagents mixed in equal volumes were added to produce a colour reaction and the plates were incubated for 30 min protected from light. The colour reaction was stopped with 2 N sulphuric acid. The absorbance at 450 nm was measured with a microplate reader (Model Sunrise, TECAN, Germany) to determine BDNF concentration according to the standard curve. Wavelength correction was conducted on 540 nm. Intra-assay coefficient of variation (CV) in our sample was 3.7%. Plasma probes of each patient (BL-EP) were analysed on one ELISA plate.

BDNF-Gene Exon-IV Methylation Status Measurements

Bisulfite Sequencing of the BDNF Exon IV Promoter Region

Genomic DNA was extracted from whole frozen EDTA-blood (200 µl) with the QIAamp® DNA Blood Mini Kit (QIAGEN GmbH, Hilden, Germany) according to the manufacturer's protocol. Afterwards, 500 ng of genomic DNA were modified by sodium-bisulfite using the EpiTect® 96 Bisulfite Kit (QIAGEN). The procedure of bisulfite conversion deaminates cytosines to uracils whereas methylated cytosines are protected from alteration. Bisulfite converted DNA was purified using a BioMek NX$^P$ liquid handling system (Beckman Coulter GmbH, Krefeld, Germany).

Primers were designed to amplify a region covering a fragment of 277 base pairs (from −200 to +77 bp relative to the starting base pair of the fourth exon of BDNF (NCBI NC_000011.9: 27723103-27723380) containing 13 CpG dinucleotides within the promoter region of BDNF-exon IV.

To amplify a specific product, a semi-nested PCR was performed using 1 µl bisulfite modified DNA or PCR round 1 product with 0.4 µl of each primer and 5 µl HotStarTaq Master Mix (Qiagen) filled to a reaction volume of 10 µl. Cycle conditions were: hot start initiation: 15 min, 95° C.; 33 cycles: denaturation: 30 sec, 95° C.; annealing 90 sec, 58.5° C.; extension 150 sec, 72° C. in both PCR rounds. All PCRs were performed on a C1000™ Thermal Cycler (Bio-Rad, Hercules Calif., USA). Primer sequences were as follows:

```
BDNF_IV_forw1:
                                    (SEQ ID NO. 2)
5'-GGGGGAGGATTAATTGAGTTAGTTTTG-3'

BDNF_IV_forw2:
                                    (SEQ ID NO. 3)
5'-TTTGTTGGGGTTGGAAGTGAAAAT-3'

BDNF_IV_rev:
                                    (SEQ ID NO. 4)
5'-ATA TAT ACT CCT TCT ATT CTA CAA CAA-3'

BDNF_IV_seq:
                                    (SEQ ID NO. 5)
5'-ACAAAAAAATTTCATACTAA-3'
```

Subsequently 10 µl of each PCR product were visualized on a standard 2.0% agarose gel and the remaining 40 µl were purified using Agencourt® AMPure®XP magnetic beads on a BioMek NX$^P$ liquid handling system (Beckman Coulter). Sequencing of the reverse strand was performed using a BigDye® Terminator v3.1 Cycle Sequencing Kit (Applied Biosystems, Foster City, Calif., USA) on an Applied Biosystems® 3500xL Genetic Analyzer (Applied Biosystems; POP-7™ polymer) according to the manufacturer's instructions. 6.9 µl of purified PCR product were applied for the extension reaction. The obtained sequences were analyzed using the ESME algorithm especially designed for determining the DNA methylation levels from the sequence trace files. Briefly, ESME performs quality control, normalizes signals, corrects for incomplete bisulfite conversion, and maps positions in the trace file to CpGs in the reference sequence by comparing the C to T (forward sequence) and G to A (reverse sequence) peaks at CpG-sites.

Insert Amplification

Genomic DNA was isolated from human venous blood using the QIAamp DNA Blood Kit (Qiagen, Hilden). The promoter region of BDNF exon IV (chr11:27722840-27723980) was amplified by PCR using Kod Polymerase (Novagen, Merck Chemicals, Darmstadt, Germany), primers BDNFpromF_361 and BDNFpromR_362 (table 1) and 100 ng DNA. PCR steps were performed as followed: 95° C. 2 min; 95° C. 20 sec, 72° C. 10 sec, 70° C. 23 sec (30 cycles). The 1141 bp fragment was determined by Sanger sequencing using BigDyeTerminator v3.1 Cycle Sequencing Kit (BDT v3.1) on an 3500xL genetic analyzer (both: Applied Biosystems, Austin, Tex.). Vector-specific sequences were adapted by re-amplification in PCR with primers INpGL4.14_F_366 and INpGL4.14_R_378 (table 4). PCR steps were: 95° C. 2 min; 95° C. 20 sec, 53° C. 10 sec, 70° C. 23 sec (6 cycles); 95° C. 20 sec, 82° C. 10 sec (incr. −0.5° C./cycle), 70° C. 23 sec (30 cycles).

Cloning of Luciferase Expression Vectors

The 1172 bp fragment with adapter sequences was cloned into HindIII HF-linearized pGL4.14[luc2/Hygro] firefly luciferase reporter plasmid (Promega, Madison, Wis.) by recombination using InFusion HD Enzyme (Clontech Laboratories Inc., Mountain View, Calif.) with a ratio of 50 ng vector:50 ng insert. Dam-/dcm-competent E. coli (New England Biolabs, Ipswich, Mass.) were transformed with 5 µL recombined plasmid and plated on LB-Agar containing 100 µg/mL Ampicillin (Carl Roth, Karlsruhe). Grown colonies were transferred to 3 mL LB-Amp-Medium and plasmids were isolated using the NucleoSpin Plasmid Kit (Macherey & Nagel, Düren). After verifying the plasmids containing the hBDNF IV promoter region by sequencing with primers pGL4.14seq_F_380 and pGL4.14seq_R_381 (table 1) and BDT v3.1, the plasmid #53-2 was amplified in dam-/dcm-deficient bacteria to reduce bacteria-specific methylation. DNA-purification was endotoxine-free (NucleoBond Xtra Midi EF Kit; Macherey & Nagel, Düren).

In Vitro-Methylation of BDNF IV Promoter Construct

The BDNF IV promoter reporter plasmid #53-2 (4 µg) was incubated (4 h 37° C.) with Sss1 DNA methyltransferase (20U; New England Biolabs, Ipswich, Mass.) in buffer containing 640 µM S-adenosylmethionine (New England Biolabs, Ipswich, Mass.). DNA was purified with Nucleospin Plasmid Kit (Macherey & Nagel, Düren).

Cell Culture Procedures

Human neuroblastoma cell-line SH-Sy5Y (ATCC, Wesel) was cultured in DMEM-Ham's F12 medium 1:1 (Biochrom AG, Berlin) supplemented with 10% FBS Superior (Biochrom AG, Berlin) and 1% penicillin/streptomycin (PAN Biotech GmbH, Aidenbach). Cells were maintained at 37° C. in a humidified atmosphere of 5% CO2 in atmosphere. To determine cytotoxic concentrations of fluoxetine and venlafaxine by CellTiter-Glo Luminescent Cell Viability Assay (Promega, Madison, Wis.) 1.5×10$^5$ cells were plated in 96 well plates and grown for 24 hours. Three wells at a time were incubated with different amounts of fluoxetine hydrochloride or venlafaxine hydrochloride (both Sigma-Aldrich Germany, Taufkirchen), both solved in sterile deionized water at 4 mg/mL. Concentrations were 5 μM, 10 μM, 25 μM, 50 μM, 75 μM, 100 μM and 0 μM as control for both fluoxetine and venlafaxine in full growth medium. After incubation for 24 hours cytotoxicity was documented by microscope photography and measured using a GloMax Multi+ Detection System (Promega, Madison, Wis.).

Transfection and Luciferase-Based Reporter Gene Assays 1.5×10$^5$ SH-Sy5Y cells were plated in 96 well plates 24 hours before transfection. 98 ng/well of BDNF IV promoter luciferase reporter plasmid #53-2 or methylated BDNF IV promoter luciferase reporter plasmid #53-2 meth were cotransfected with 2 ng/well pGL4.74 [hRluc/TK] renilla luciferase control plasmid (Promega, Madison, Wis.) to enable normalization (3 columns per reporter plasmid). FuGene HD Transfection Reagent (Promega, Madison) was applied in a ratio 3:1. Basal medium without antibiotics was used until medium exchange after 5 hours, where full growth medium supplemented with the following non-toxic drug concentrations was added: 3 μM, 5 μM, 10 μM Fluoxetine or 10 μM, 30 μM, 50 μM Venlafaxine (one concentration/row), control: 0 μM. After incubation over 48 hours cells were lysed and luminescence was measured using the Dual Luciferase Reporter Assay System (Promega, Madison) and the GloMax Multi+ Luminometer (Promega, Madison), according to the manufacturer's protocol.

Statistical Analysis

Normal distribution of hypothesis for all variables was tested using Kolmogorov-Smirnov's test and afterwards descriptive statistics were performed as appropriate (mean, median, standard deviation, quartiles). To analyze if DNA methylation levels change during treatment, we used linear mixed modelling with methylation as dependent variable and time as repeated factor (best fit model with scaled identity as covariate structure) and CpG position as fixed factor and time x CpG interaction. We included the patient's ID as random factor to account for inter-individual variation in methylation levels. Study participants were categorized according to the above mentioned HAM-D criteria into Responder/Non-responder and Remitter/Non-remitters respectively at study endpoint. Differences in baseline DNA methylation between these groups were analyzed using the Mann-Whitney-U test. P-values were adjusted for the 13 CpG's measured per patient. CpG's showing differences between groups were further analyzed using receiver-operator characteristics and were dichotomized with different cut-off values (1. no methylation vs. any methylation; 2. Youden's index; 3. Median split). Fisher's exact tests were calculated to obtain possible differences between dichotomized CpG measures and remission or response status. Multiple logistic regression analyses using remission or response as dependent and CpG methylation (continuous or dichotomized) as independent variables and Odd's ratios were calculated. To determine predictive properties of different CpGs we calculated sensitivity, specificity and positive or negative predictive values using Bayes' formula. All analyses were performed using IBM® SPSS® Statistics 19 for Windows (IBM Corporation, Armonk N.Y., USA).

TABLE 3

Methylation status of responders and non-responders for different CpGs

| CpG | Median of methylated C fraction in responders | Median of methylated C fraction in non-responders | Median of methylated C fraction in remitters | Median of methylated C fraction in non-remitters |
|---|---|---|---|---|
| CpG-87 | 0.03 | 0.00 | 0.04 | 0.00 |
| CpG-148 | 0.08 | 0.07 | 0.07 | 0.07 |
| CpG-111 | 0.10 | 0.09 | 0.10 | 0.09 |
| CpG-66 | 0.04 | 0.02 | 0.07 | 0.02 |
| CpG-58 | 0.13 | 0.08 | 0.11 | 0.08 |
| CpG-35 | 0.05 | 0.03 | 0.02 | 0.04 |
| CpG-24 | 0.02 | 0.00 | 0.02 | 0.00 |
| CpG + 42 | 0.26 | 0.00 | 0.26 | 0.00 |

TABLE 4

Oligonucleotides used as primers (Metabion, Martinsried)

| Name | Sequence (5'→3') |
|---|---|
| BDNF4promR_362 | CCCACCTTTTCAGTCACTACTTGTCAAAGT AACC (SEQ ID NO. 6) |
| BDNF4promF_361 | TTCCTCTGATACCCAGTGTTGTACCCCAA GA (SEQ ID NO. 7) |
| INpGL4.14_F_366 | TGGCCTCGGCGGCCA TTCCTCTGATACCC AGTGT (SEQ ID NO. 8) |
| INpGL4.14_R_378 | CCGGATTGCCAAGCT CCCACCTTTTCAGT CACT (SEQ ID NO. 9) |
| pGL4.14seq_F_380 | TGGCCGGTACCTGAGCTCGCTA (SEQ ID NO. 10) |
| pGL4.14seq_R_381 | GCATCTTCCATGGTGGCTTTA (SEQ ID NO. 11) |
| bisBDNF_IV_forw1: | GGGGGAGGATTAATTGAGTTAGTTTTG (SEQ ID NO. 2) |
| bisBDNF_IV_forw2: | TTTGTTGGGGTTGGAAGTGAAAAT (SEQ ID NO. 3) |
| bisBDNF_IV_rev: | ATA TAT ACT CCT TCT ATT CTA CAA CAA (SEQ ID NO. 4) |
| BDNF_IV_seq: | ACAAAAAAATTTCATACTAA (SEQ ID NO. 5) |

Results and Discussion

The methylation data for different CpG dinucleotides show the predictive value for the response or non-response and remission or non-remission (Table 3). As further exemplified for CpG-87 the methylation status of BDNF-gene promoters allow the prediction of non-response or response to a monoaminergic drug The data for CpG-87 clearly demonstrates that the methylation status is predictive for the response or non-response and remission or non-remission within six weeks after treatment with a monoaminergic antidepressant (FIGS. 1 and 2). It could furthermore been shown that the methylation of CpG-87 is associated with an early increase of BDNF plasma levels after 1 week of treatment with a monoaminergic antidepressant (FIG. 3).

In order to verify that DNA methylation of the BDNF-gene exon-IV promoter in MDD patients affects antidepressant treatment response, we determined the methylation status in leucocytes of 13 CpGs within the BDNF-gene exon-IV promoter (Keller et al. (2010) Arch Gen Psychiatry, 67: 258-67) in the same sample of patients with major depression, which has served for the investigation of the impact of early peripheral BDNF changes on final response to antidepressant pharmacotherapy (Tadićet al. (2011) Prog Neuropsychopharmacol Biol Psychiatry, 35: 415-420; Dreimüller et al. (2012) Neuropharmacology, 62: 264-269). The Intention-to-Treat sample consisted of 46 patients with MDD (Tadić et al. (2011) Prog Neuropsychopharmacol Biol Psychiatry, 35: 415-420; Dreimüller et al. (2012) Neuropharmacology, 62: 264-269); due to missing methylation data at baseline [BL] in seven patients the final sample consisted of 39 patients (mean age±SD=44.9±12.7; mean HAMD-21 sum score at baseline±SD=20.4±4.5). Of the 13 investigated CpG sites 12 yielded sufficient measurements; the CpG at position +42 was dropped from the analysis. The baseline methylation status at CpG position −87 predicted antidepressant non-response: final non-responders had a significantly lower methylated C fraction than final responders (FIG. 4A). Patients without methylation at CpG site −87 had a significantly higher risk for non-response than those with any methylation (FIG. 4B). These differences were also found for final non-remission with a similar effect size (data not shown). Furthermore, patients with an unmethylated CpG site −87 showed a decrease of plasma BDNF levels during the first week of treatment with a trend towards significance (FIG. 4C). DNA methylation of the 12 investigated CpG sites in BDNF-gene exon-IV promoter did not change significantly during antidepressant treatment (FIG. 4D).

For further analysis, we cloned the BDNF-gene exon-IV promoter fragment into a pGL4 luciferase expression vector and tested the effect of methylation of the whole vector on antidepressant induced changes in luciferase expression in a neuroblastoma cell line (SH-SY5Y). We found a significant decrease of luciferase expression after 48 h incubation with fluoxetine or venlafaxine in the unmethylated fragment only, whereas antidepressants did not change expression levels when the promoter fragment was methylated (FIG. 4E).

Our results are supported by a strong neurobiological framework linking antidepressant response to the ability of an antidepressant to increase BDNF expression. Apart from the well known pathway via cAMP mediated CREB activation, antidepressants can also increase BDNF expression via phosphorylation of methyl CpG binding protein 2 (MeCP2) which—in its unphosphorylated form—binds to the promoter and forms a repressor complex but dissociates from the DNA upon phosphorylation (Hutchinson et al. (2012) J Neurosci, 32:14355-63). Thus, as methylation of the promoter is a prerequisite for specific MeCP2 binding, our results suggest that this leg of antidepressant action on BDNF can only be active in carriers of methylation at the relevant CpG site within the promoter. Our results derived from a clinical study in MD patients were corroborated by an established in-vitro system analysis; nevertheless, they are preliminary and must be confirmed by independent samples with consistent medication treatment and alternative methods. Additional effort is required to disentangle the relation between Major Depression, methylation of BDNF-gene exon-IV promoter and MeCP2 dissociation following antidepressant treatment, as this finally might lead to biomarker-guided treatment of MD.

Without been bound by theory, this is explained by the methylation of CpG−87 being a prerequisite for MeCP2-binding at the BDNF promoter. It is believed that MeCP2 represses the transcription of BDNF and gets phosphorylated after treatment with antidepressants. Phosphorylated MeCP2 dissociates from the BDNF promoter thereby stopping the repression of BDNF expression. Furthermore, CREB is phosphorylated and gets activated on treatment with antidepressants. The data presented suggests that the binding of MeCP2 to the BDNF promoter is depended on methylated CpG dinucleotides, e.g. CpG−87. The hypomethylation of said CpG dinucleotides causes the absence of MeCP2 binding to the promoter and the influence of MeCp2 phosphorylation is abolished causing an early increase in BDNF plasma levels.

Hence, the data presented for the first time shows that the methylation status of a BDNF-gene promoter is predictive for the non-response or response of a patient to a monoaminergic antidepressant.

The invention claimed is:

1. A method of determining the hypomethylation status of a CpG island in human brain-derived neurotrophic factor (BDNF)-gene promoter in a patient, wherein said method comprises:
   (a) performing a DNA methylation status assay to detect the level of DNA-methylation of CpG-87 of exon-IV of the human BDNF-gene promoter in a sample derived from the patient,
   (b) assaying for the hypomethylation status of CpG-87 by determining the methylated cytosine (C) fraction of CpG-87;
   wherein a hypomethylated CpG-87 is less than 0.05 and wherein said patient is suffering from depression, major depressive disorder, mild depression, panic disorder, social anxiety disorder, social phobia, bulimia nervosa, obsessive-compulsive disorder, post-traumatic stress disorder, or generalized anxiety disorder.

2. The method of claim 1, wherein said patient is reported as a non-responder to a monoaminergic antidepressant.

3. The method of claim 1, wherein a methylated C fraction of 0.05 or greater at CpG-87 in the sample is reported and said patient is reported as a responder to a monoaminergic antidepressant.

4. The method of claim 3, wherein the method further comprises administering to the patient having a methylated C fraction of 0.05 or greater at CpG-87 a monoaminergic antidepressant selected from a serotonin reuptake inhibitor (SSRI), a selective serotonin and noradrenalin reuptake inhibitor (SNRI), a selective noradrenaline and dopamine reuptake inhibitor, a selective norepinephrinedopamine reuptake inhibitor, a monoamine oxidase inhibitor, a tricyclic antidepressant, or monoaminergic antidepressants.

5. The method of claim 3, wherein the method further comprises administering to the patient having a methylated C fraction of 0.05 or greater at CpG-87 a monoaminergic antidepressant selected from venlafaxin, sertralin, mirtazapin, escitalopram, citalopram, fluoxetine, paroxetin, duloxetin, bupropion, amitriptylin, clomipramin, trimipramin, tranylcypromin or agomelatine.

6. The method of claim 1, wherein the DNA methylation status assay is selected from bisulfite sequencing, pyrosequencing, MALDI-TOF, methylation sensitive enzymatic digestion, or qMSP.

7. The method of claim 1, wherein the method is performed before administration of a monoaminergic antidepressant.

8. The method of claim 1, wherein the sample is obtained from blood, serum, plasma, saliva, sputum or cerebrospinal fluid.

9. The method of claim 1, wherein the method further comprises determining the DNA-methylation status of at least one additional CpG island of human BDNF gene promoter selected from CpG-148, CpG-111, CpG+18, CpG-66, CpG-58, CpG-35, CpG-39, CpG-24, CpG-11, CpG+20, CpG+36, CpG+42, CpG+51, and CpG+54.

10. The method of claim 9, wherein the method further comprises determining the methylated C fraction of at least one additional CpG island of human BDNF gene promoter selected from CpG-148, CpG-111, CpG+18, CpG-66, CpG-58, CpG-35, CpG-39, CpG-24, CpG-11, CpG+20, CpG+36, CpG+42, CpG+51, and CpG+54.

11. The method of claim 10, wherein the CpG island is further reported to be hypomethylated if the methylated C fraction of the CpG island is selected from:
   a. CpG-148 of less than 0.10;
   b. CpG-111 of less than 0.12;
   c. CpG+18 of less than 0.03;
   d. CpG-66 of less than 0.05;
   e. CpG-58 of less than 0.12;
   f. CpG-35 of less than 0.04;
   g. CpG-39 of less than 0.05;
   h. CpG-24 of less than 0.02;
   i. CpG-11 of less than 0.02;
   j. CpG+20 of less than 0.02;
   k. CpG+36 of less than 0.02; or
   l. CpG+42 of less than 0.26.

12. The method of claim 1, wherein the method comprises determining the DNA-methylation status of CpG-87, CpG-66 and CpG-58.

13. The method of claim 1, wherein the DNA methylation status assay comprises contacting the DNA in the sample with bisulfite or sodium bisulfite.

* * * * *

UNITED STATES PATENT AND TRADEMARK OFFICE
CERTIFICATE OF CORRECTION

PATENT NO. : 10,059,996 B2
APPLICATION NO. : 14/406983
DATED : August 28, 2018
INVENTOR(S) : Helge Frieling et al.

It is certified that error appears in the above-identified patent and that said Letters Patent is hereby corrected as shown below:

In the Claims

Column 49, Claim 4, should read:
--The method of claim 3, wherein the method further comprises administering to the patient having a methylated C fraction of 0.05 or greater at CpG-87 a moneaminergic antidepressant selected from a serotonin reuptake inhibitor (SSRI), a selective serotonin and noradrenalin reuptake inhibitor (SNRI), a selective noradrenaline and dopamine reuptake inhibitor, a selective norepinephrine-dopamine reuptake inhibitor, a monoamine oxidase inhibitor, a tricyclic antidepressant, or monoaminergic antidepressants.--

Signed and Sealed this
Sixth Day of August, 2019

Andrei Iancu
*Director of the United States Patent and Trademark Office*

UNITED STATES PATENT AND TRADEMARK OFFICE
CERTIFICATE OF CORRECTION

PATENT NO. : 10,059,996 B2
APPLICATION NO. : 14/406983
DATED : August 28, 2018
INVENTOR(S) : Helge Frieling et al.

It is certified that error appears in the above-identified patent and that said Letters Patent is hereby corrected as shown below:

In the Claims

Column 49, Claim 4, should read:
--The method of claim 3, wherein the method further comprises administering to the patient having a methylated C fraction of 0.05 or greater at CpG-87 a monoaminergic antidepressant selected from a serotonin reuptake inhibitor (SSRI), a selective serotonin and noradrenalin reuptake inhibitor (SNRI), a selective noradrenaline and dopamine reuptake inhibitor, a selective norepinephrine-dopamine reuptake inhibitor, a monoamine oxidase inhibitor, a tricyclic antidepressant, or monoaminergic antidepressants.--

This certificate supersedes the Certificate of Correction issued August 6, 2019.

Signed and Sealed this
First Day of September, 2020

Andrei Iancu
*Director of the United States Patent and Trademark Office*

SEQUENCE LISTING

<160> NUMBER OF SEQ ID NOS: 11

<210> SEQ ID NO 1
<211> LENGTH: 278
<212> TYPE: DNA
<213> ORGANISM: Homo sapiens
<220> FEATURE:
<221> NAME/KEY: source
<222> LOCATION: 1..278
<223> OTHER INFORMATION: /mol_type="unassigned DNA"
    /organism="Homo sapiens"

<400> SEQUENCE: 1

```
tttgctgggg ctggaagtga aaacatctgc aaaagcatgc aatgccctgg aacggaactc      60
ttctaataaa agatgtatca ttttaaatgc gctgaatttt gattctggta attcgtgcac     120
tagagtgtct atttcgaggc agcggaggta tcatatgaca gcgcacgtca aggcaccgtg     180
gagccctctc gtggactccc acccactttc ccattcaccg cggagagggc tgctctcgct     240
gccgctcccc ccggcgaact agcatgaaat ctccctgc                             278
```

<210> SEQ ID NO 2

```
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="unassigned DNA"
      /note="BDNF_IV_forw1 primer"
      /organism="Artificial Sequence"

<400> SEQUENCE: 2
gggggaggat taattgagtt agttttg                                          27

<210> SEQ ID NO 3
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="unassigned DNA"
      /note="BDNF_IV_forw2 nested primer"
      /organism="Artificial Sequence"

<400> SEQUENCE: 3
tttgttgggg ttggaagtga aaat                                             24

<210> SEQ ID NO 4
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="unassigned DNA"
      /note="BDNF_IV_rev primer"
      /organism="Artificial Sequence"

<400> SEQUENCE: 4
atatatactc cttctattct acaacaa                                          27

<210> SEQ ID NO 5
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="BDNF_IV_seq primer"
      /organism="Artificial Sequence"

<400> SEQUENCE: 5
acaaaaaaat ttcatactaa                                                  20

<210> SEQ ID NO 6
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="unassigned DNA"
      /note="BDNF4promR_362"
      /organism="Artificial Sequence"

<400> SEQUENCE: 6
cccacctttt cagtcactac ttgtcaaagt aacc                                  34
```

```
<210> SEQ ID NO 7
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
      /note="BDNF4promF_361"
      /organism="Artificial Sequence"

<400> SEQUENCE: 7
ttcctctgat acccagtgtt gtacccccaa ga                            32

<210> SEQ ID NO 8
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /mol_type="unassigned DNA"
      /note="INpGL4.14_F_366"
      /organism="Artificial Sequence"

<400> SEQUENCE: 8
tggcctcggc ggccattcct ctgatacccca gtgt                         34

<210> SEQ ID NO 9
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
      /note="INpGL4.14_R_378"
      /organism="Artificial Sequence"

<400> SEQUENCE: 9
ccggattgcc aagctcccac cttttcagtc act                           33

<210> SEQ ID NO 10
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="pGL4.14seq_F_380"
      /organism="Artificial Sequence"

<400> SEQUENCE: 10
tggccggtac ctgagctcgc ta                                       22

<210> SEQ ID NO 11
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="pGL4.14seq_R_381"
      /organism="Artificial Sequence"

<400> SEQUENCE: 11
gcatcttcca tggtggcttt a                                        21
```